US006304328B1

(12) United States Patent
Longtin

(10) Patent No.: US 6,304,328 B1
(45) Date of Patent: *Oct. 16, 2001

(54) NON-CONTACT TEMPERATURE AND CONCENTRATION MEASUREMENT ON LIQUID SURFACES

(75) Inventor: Jon P. Longtin, East Setauket, NY (US)

(73) Assignee: Research Foundation of State University of New York, The Office of Technology Licensing, SUNY, Stony Brook, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/134,201

(22) Filed: Aug. 14, 1998

(51) Int. Cl.[7] ..................................................... G01N 21/55
(52) U.S. Cl. .............................................. 356/445; 39/372
(58) Field of Search ............................... 356/445, 39, 372

(56) References Cited

U.S. PATENT DOCUMENTS

| | | | |
|---|---|---|---|
| 5,209,231 | * | 5/1993 | Cote et al. ............................ 356/367 |
| 5,510,267 | * | 4/1996 | Marshall ............................ 356/39 X |
| 5,748,318 | * | 5/1998 | Mavis et al. ......................... 356/381 |

OTHER PUBLICATIONS

T.L. Bergman, "Measurement of Salinity Distributions in Salt–Stratified, Double–Diffusive Systems by Optical Deflectometry," Rev. Sci. Instrum., 57(10), pp. 2538–2542, Oct. 1986.

(List continued on next page.)

Primary Examiner—Frank G. Font
Assistant Examiner—Reginald A. Ratliff
(74) Attorney, Agent, or Firm—BakerBotts L.L.P.

(57) ABSTRACT

An apparatus and method for temperature and concentration measurement at liquid surfaces using reflectance. The apparatus includes a light source which produces a measurement light beam, and also includes a detector. The measurement light beam has a measurement light beam intensity and impinges on the surface of the liquid specimen. It reflects back as a reflected light beam with a reflected light beam intensity which is related to the reflectivity R of the liquid surface and to the measurement light beam intensity. The detector receives the reflected light beam and determines the reflected light beam intensity. Either the temperature or concentration of the liquid specimen can then be determined based on the reflected light beam intensity. The light source can be a coherent light source, such as a laser. A beam splitter can be provided to split the light beam from the light source into a reference light beam and the measurement light beam. The reference light beam is used to compensate for fluctuations in the light source. Temperature measurements can be conducted on a pure liquid or a multi-component liquid with a substantially constant concentration. Concentration measurements can be conducted on a multi-component liquid which is maintained in a substantially isothermal condition. The method of the invention includes causing a measurement light beam with a measurement light beam intensity to impinge on the surface of the liquid specimen; detecting a reflected light beam; and determining either the temperature or the concentration of the liquid specimen. The measurement light beam can be caused to impinge on the surface of the liquid at an angle which enhances the change of reflectivity with respect to temperature or concentration. Detection of the intensity of the light beams can be carried out using photodiodes, amplifier circuitry, and relatively low-cost digital voltmeters.

30 Claims, 13 Drawing Sheets

Microfiche Appendix Included
(1 Microfiche, 16 Pages)

OTHER PUBLICATIONS

Bergman et al., "Miniature Fiber–Optic Refractometer for Measurement of Salinity in Double–Diffusive Thermohaline Systems," Rev. Sci. Instrum., 56(2), pp. 291–296, Feb. 1985.

Lee et al., "A New Optical Method For Measuring Surface Temperature at Large Incident Probe Angles," Rev. Sci. Instrum., 68(2), pp. 1307–1311, Feb. 1997.

Qiu et al., "Novel Technique for NonContact and Microscale Temperature Measurements," Experimental Heat Transfer, vol. 6, pp. 231–241, (1993).

J. Stone, "Measurements of the Absorption of Light in Low–Loss Liquids," Journal of the Optical Society of America, vol. 62, No. 3, pp. 327–333, Mar. 1972.

Chen et al., "Noncontact Nanosecond–Time–Resolution Temperature Measurement in Excimer Laser Heating of Ni–P Disk Substrates," Appl. Phys. Lett. 71(22), pp. 3191–3193, Dec. 1997.

* cited by examiner

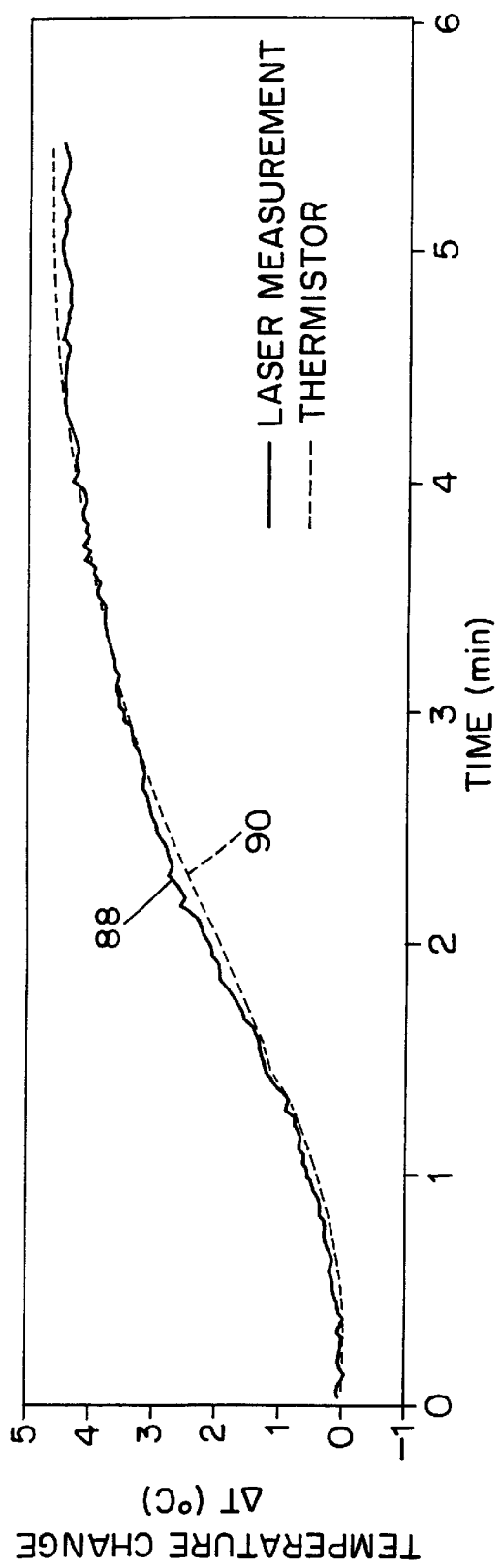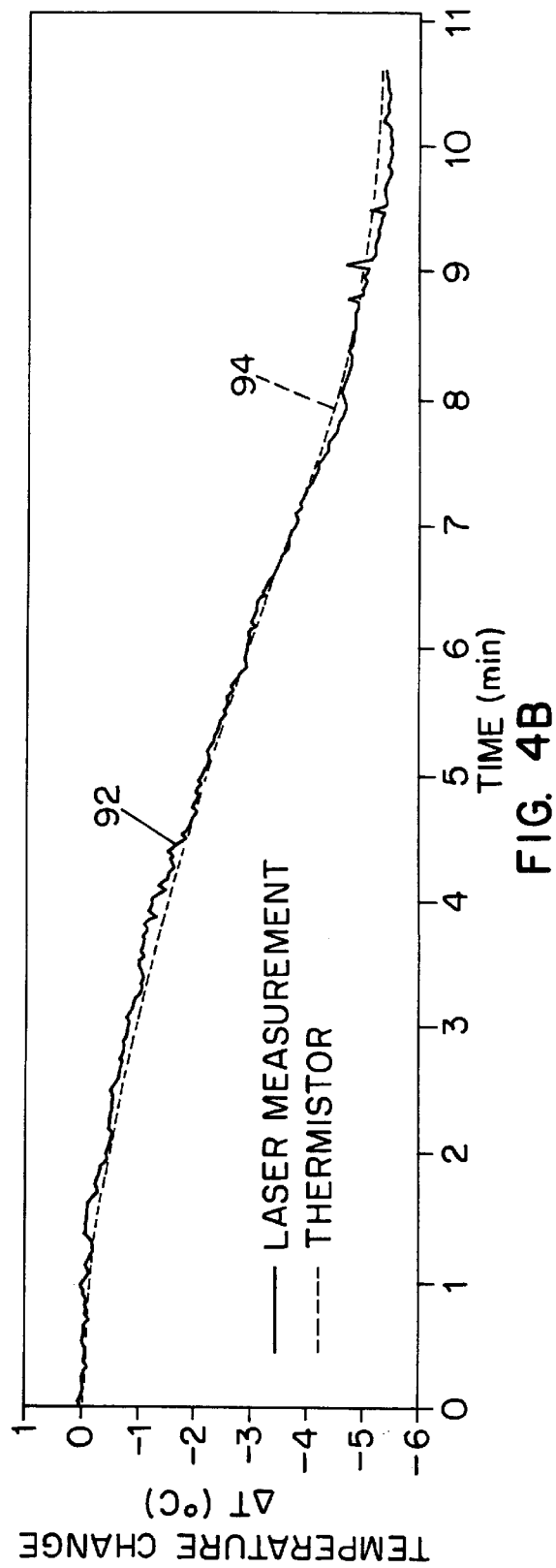
FIG. 4A
FIG. 4B

NON-CONTACT TEMPERATURE AND CONCENTRATION MEASUREMENT ON LIQUID SURFACES

STATEMENT OF GOVERNMENT RIGHTS

This invention was made with government support under National Science Foundation Contract No. CTS-9702644. The government may have certain rights in the invention.

Pursuant to 37C.F.R. 1.96 (c) this patent includes an appendix which will not be printed but is available on one microfiche (16 frames).

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

1. Field of the Invention

The present invention relates to temperature and concentration measurement, and more particularly relates to non-contact temperature and concentration measurement on liquid surfaces using reflectance techniques.

2. Brief Description of the Prior Art

It is desirable to measure temperature at a liquid surface for a number of applications. For multi-component liquids, it is also desirable to measure concentration. Although the surface temperature and concentration are important parameters, it has proven difficult to measure them with conventional techniques.

Some prior measurement techniques rely on direct-contact; i.e., a sensor or probe must come in contact with the liquid to be measured. Such measurement techniques, however, have the drawbacks of the potential for contamination; the inconvenience of introducing a probe into the liquid to be measured; and the invasive nature of the measurement which may influence the process being measured.

Accordingly, there has been interest in non-contact measurement techniques. One well-known prior method is use of a commercial infrared thermometer. Such thermometers exhibit poor accuracy for measurement of temperature of surfaces where the emissivity is not close to unity, for example, liquids and highly reflective metals.

In an effort to overcome the problems associated with infrared surface temperature measurement, efforts have been made to develop laser-based techniques. Such techniques have been disclosed in the following publications: T. Q. Qiu et al., "Novel Technique for Noncontact and Microscale Temperature Measurements," *Experimental Heat Transfer*, v.6, 231–41 (1993); A. S. Lee et al., "Temperature Measurement by Thermoreflectance at Near Grazing Angles," *Proceedings of the 1996 A.S.M.E. International Mechanical Engineering Congress and Exposition*, v.59, 77–82 (Atlanta, Ga., Nov. 17–22, 1996); and A. S. Lee and P. M. Norris, "A New Optical Method for Measuring Surface Temperature and Large Incident Probe Angles," *Rev. Sci. Instrum.*, v.68, 1307–11 (1997). However, these prior techniques have focused almost exclusively on temperature measurement of surfaces of solid-state materials; relatively little attention has been paid to liquids.

Optical techniques for measuring concentration in liquids have been known previously. One paper discloses an optical probe which relies on changes in the index of refraction to measure liquid concentration. T. L. Bergman, "Miniature Fiber-Optic Refractometer for Measurement of Salinity in Double-Diffusive Thermohaline Systems," *Rev. Sci. Instrum.*, v.56, 291–96 (1985). However, the techniques set forth in this paper still require immersion of a probe in the liquid. Measurement of salt concentration based on the image distortion of a fine wire as it passes through a variable-concentration liquid has also been disclosed. T. L. Bergman, "Measurement of Salinity Distributions in Salt-Stratified, Double-Diffusive Systems by Optical Deflectometry," *Rev. Sci. Instrum.*, v.57, 2538–42 (1986). This technique measures concentration in the bulk liquid as an integrated effect of concentration variation along the light path. Again, however, immersion of a sensor, in this case, the fine wire, was required with the attendant disadvantages.

In view of the foregoing deficiencies with current techniques for measurement of temperature and concentration at a liquid surface, it would be desirable to develop an apparatus and method for non-contact temperature and concentration measurement on liquid surfaces. In addition to affording a non-invasive measurement technique, it would be desirable if the apparatus and method permitted remote monitoring and location of test and analysis equipment, imperviousness to harsh and corrosive environments, and very high spatial precision. Yet further, it would also be desirable if the apparatus and method were capable of fast response times and high reliability and repeatability.

SUMMARY OF THE INVENTION

The present invention, which addresses the shortcomings of the current systems, provides an apparatus for non-contact measurement of either the temperature or, for multi-component systems, the concentration at a surface of a liquid specimen. The apparatus includes a light source which produces a measurement light beam, and a detector. A container for the liquid specimen can optionally be provided. The measurement light beam has a measurement light beam intensity, and impinges on the surface of the liquid specimen and reflects back as a reflected light beam with a reflected light beam intensity. The reflected light beam intensity is related to both the reflectivity, R, of the liquid surface and to the measurement light beam intensity. The detector receives the reflected light beam and determines either the temperature or the concentration of the liquid specimen based on the reflected light beam intensity.

The light source can be a coherent light source. For temperature measurement, the liquid is preferably either a single component liquid or a multi-component liquid with a substantially constant concentration. Conversely, for concentration measurement, the liquid is a multi-component liquid which is preferably maintained in a substantially isothermal condition.

For temperature measurement, a temperature change of the liquid is determined from the equation:

$$\Delta R = (dR/dn)(\partial n/\partial T)\Delta T$$

where:

$\Delta R$ is a change in the reflectivity of the liquid from a reference state as determined from the reflected light beam intensity and the measurement light beam intensity, n is the index of refraction of the liquid, dR/dn is the first derivative of the reflectivity with respect to n, T is the temperature of the liquid, ∂n/∂T is the first derivative of n with respect to the temperature, ΔT is a change in the temperature of the liquid from a known initial value, $R=((n-1)/(n+1))^2$, and $dR/dn=4(n-1)/(n+1)^3$.

Similarly, for concentration measurement, a change in concentration of the liquid is determined using the formula:

$$\Delta R = (dR/dn)(\partial n/\partial C)\Delta C$$

where:

ΔR is a change in the reflectivity of the liquid from a reference state as determined from the reflected light beam intensity and the measurement light beam intensity, n is the index of refraction of the liquid, dR/dn is the first derivative of the reflectivity with respect to n, C is the concentration of the liquid system expressed on a volume or mass basis, ∂n/∂C is the first partial derivative of n with respect to the concentration (expressed consistently with C), ΔC is a change in the concentration of the liquid from a known initial value, $R=((n-1)/(n+1))^2$, and $dR/dn=4(n-1)/(n+1)^3$.

A beam splitter can be provided to split off a reference beam in order to account for fluctuations in intensity of the light source. Intensity of the reflected and reference beams can be determined using photodetectors such as photodiodes, suitable transresistance amplifiers, and digital voltmeters. If desired, output from the voltmeters can be input to a computer which performs required calculations.

A method, according to the present invention, for non-contact measurement of one of temperature and concentration at a surface of a liquid specimen includes the steps of causing a measurement light beam to impinge on the surface of the liquid and to reflect back as a reflected light beam; detecting the reflected light beam; and determining either the temperature or the concentration of the liquid specimen based on the intensity of the reflected light beam. The reflected light beam intensity can be measured when the reflected light beam is detected. The reflected light beam intensity is related to both the reflectivity, R, of the liquid surface and to the intensity of the measurement light beam.

The method can also include the additional step of providing a coherent light source, such that the measurement light beam is coherent and emanates from the coherent light source.

As for the apparatus, for temperature measurement, the liquid should be either a single-component liquid or a multi-component liquid with a substantially constant concentration. Again, for concentration measurement, the liquid is a multi-component liquid preferably maintained in a substantially isothermal condition. The same equations relating ΔT and ΔC to ΔR are used in the method as set forth above for the apparatus.

The method can include the additional steps of determining an effective initial value for the reflected light beam intensity, in the form of a reflected light beam voltage signal, based on a voltage signal corresponding to the intensity of the reference light beam (which can be provided as for the apparatus) and from a relationship between the reference light beam voltage signal and the reflected light beam voltage signal evaluated in a substantially unperturbed state, i.e., in the absence of substantial temperature or concentration changes.

The present invention thus provides an apparatus and method for laser-based temperature and concentration measurement at liquid surfaces which overcome the disadvantages of prior systems and methods. In particular, the present method and apparatus permit non-invasive measurements, exhibit imperviousness to harsh and corrosive environments, afford rapid response times, and have remote monitoring potential. Accordingly, test and analysis equipment can also be remotely located. High spatial precision, high reliability and repeatability are all obtainable. The potential for contamination is avoided, and liquid surfaces with non-unity emissivities can be measured, unlike in infrared techniques.

These and other features and advantages of the present invention will be pointed out in the following specification, taken in connection with the accompanying drawings, and the scope of the invention will be set forth in the appended claims.

BRIEF OF DESCRIPTION OF THE DRAWINGS

FIG. 4A is similar to FIG. 3A except that the liquid is methanol;

FIG. 4B is similar to FIG. 3B except that the liquid is methanol;

DETAILED DESCRIPTION OF THE INVENTION

Figure 1:
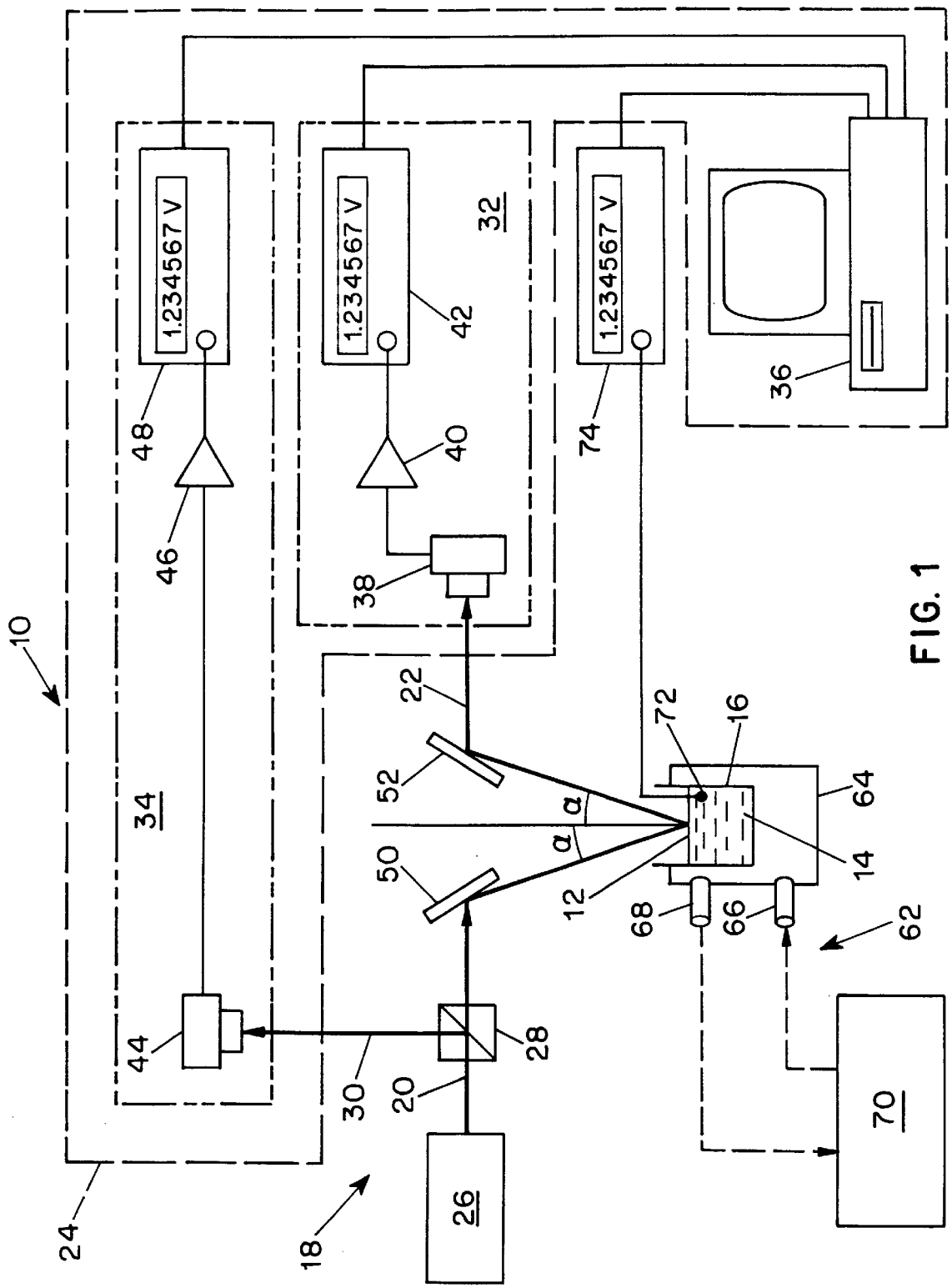
FIG. 1 is a schematic diagram of an exemplary embodiment of an apparatus according to the present invention.

Reference should now be had to FIG. 1 which depicts an apparatus for non-contact temperature and concentration measurement on liquid surfaces in accordance with the present invention, designated generally as 10. Apparatus 10 measures either the temperature or the concentration at a surface 12 of a liquid specimen 14. A container 16 which contains the liquid specimen 14 can be provided separately, or as part of apparatus 10. Apparatus 10 includes a light source, designated generally as 18, which produces a measurement light beam 20. Measurement light beam 20 has a measurement light beam intensity, and impinges on the surface 12 of the liquid specimen 14 and then reflects back as a reflected light beam 22. Reflected light beam 22 has a reflected light beam intensity related to both the reflectivity, R, of the liquid surface 12 and to the intensity of the measurement light beam 20. Apparatus 10 also includes a detector 24 which receives the reflected light beam 22 and determines either the temperature or the concentration of the liquid specimen 14 based on the intensity of the reflected light beam 22. It should be noted that the temperature or concentration measured is substantially that of the liquid at the surface; a depth of one-half wavelength is a more precise statement but such a depth might include only on the order of 1000 atomic layers.

Light source 18 can be a coherent light source such as, for example, laser 26. One suitable type of laser is a HeNe laser having a wavelength λ=632.8 nm.

Apparatus 10 can include a beam splitter 28 which splits a reference light beam 30 out of the measurement light beam 20 before the measurement light beam 20 impinges on the surface 12 of the liquid specimen 14. The reference light beam 30 has a reference light beam intensity which is indicative of the measurement light beam intensity. By this latter statement, it is meant that the intensity of the reference light beam 30 can be associated with the intensity of the measurement light beam 20 before the measurement light beam 20 impinges on the surface 12 of specimen 14.

When beam splitter 28 is employed, detector 24 also receives reference light beam 30 and also uses the intensity of reference light beam 30 to determine either the temperature or the concentration of the liquid specimen 14. The intensity of reference light beam 30 is used to compensate for fluctuations in light source 18. Further specifics regarding exemplary ways in which this compensation can be done will be set forth below. Note that measurements of the output of a typical 1mW HeNe laser, such as may be employed with the present invention, reveal minute intensity fluctuations on a 10–15 second time scale. Although small, these fluctuations are still an order of magnitude larger than the expected signal for a 1° C. temperature change (or a 1% concentration change) at the liquid surface.

For temperature measurement, liquid specimen 14 should be either a single component liquid or a multi-component liquid with a substantially constant concentration. This is because the present invention uses reflectivity, that is, the variation of index of refraction, and thus reflectance, with both temperature and concentration. To measure temperature, concentration must be held substantially constant; while to measure concentration, temperature must be held substantially constant. As used herein, "substantially constant" with respect to concentration or "substantially isothermal" with respect to temperature means that the indicated parameter has sufficiently small variations so as not to appreciably influence the measurement process for the other parameter, i.e., the other of temperature and concentration. Further explanatory details will be supplied below.

It is desirable that measurement light beam 20 impinges on the surface 12 of liquid specimen 14 at a near-normal angle of incidence α. This generally serves to maximize the percent change in reflectivity with temperature and also permits the approximations for R and dR/dn set forth below. These approximations are valid for both s- and p-polarized light at near-normal incidence.

In temperature measurement, detector 24 determines the temperature of the liquid specimen 14 according to the formula:

$$\Delta R = (dR/dn)(\partial n/\partial T)\Delta T \quad (1)$$

where:

ΔR is a change in the reflectivity of the liquid from a reference state as determined from said reflected light beam intensity and said measurement light beam intensity, n is index of refraction of the liquid, dR/dn is first derivative of the reflectivity with respect to n, T is the temperature of the liquid, ∂n/∂T is first partial derivative of n with respect to the temperature (reduces to total derivative if no substantial dependence of n on other parameters), ΔT is a change in the temperature of the liquid from a known initial value, $R = ((n-1)/(n+1))^2$, and (2)

$dR/dn = 4(n-1)/(n+1)^3$. (3)

Detector 24 can include a signal photodetector 32 which receives reflected light beam 22 and produces a reflected light beam signal in response to the intensity of reflected light beam 22. Further, detector 24 can also include a reference photodetector 34 which receives reference light beam 30 and produces a reference light beam signal in response to the intensity of reference light beam 30. Yet further, detector 24 can include a computer 36 which receives the reflected light beam signal and the reference light beam signal. Computer 36 can include a digital computer, an analog computer, or any other computing device capable of calculating the desired value of temperature (or concentration). The computer could even simply be the provision of a suitable indicating scale on, for example, a voltmeter.

Computer 36 can receive the reflected light beam signal and the reference light beam signal and can then determine the temperature of the liquid specimen 14 based on the index of refraction of the liquid specimen 14, the first derivative of the index of refraction with respect to the temperature of the liquid 14, the reflected light beam signal, and a change of the intensity of the reflected light beam 22 due to a change in the temperature of the liquid 14. The change of the intensity of the reflected light beam 22 can be determined using the reference light beam signal and the reflected light beam signal.

The liquid temperature can be determined by calculating a temperature change ΔT which is determined using the formula:

$$\Delta T = ((n^2-1)(\Delta V))/(4(\partial n/\partial T)V_{sig}) \quad (4)$$

where:

n is the index of refraction of the liquid,

∂n/∂T is the first derivative of the index of refraction with respect to the temperature of the liquid, $V_{sig}$ is the reflected light beam voltage signal, and ΔV is a difference between the reflected light beam voltage signal and an effective initial value of the reflected light beam voltage signal determined using the reference light beam voltage signal.

The signal photodetector 32 can include a signal photodiode 38 which receives the reflected light beam 22 and produces the reflected light beam signal as a reflected light beam current signal. The signal photodetector 32 can also include a signal amplifier 40 (preferably a transresistance amplifier) which is electrically coupled to the signal photodiode 38 and which is electrically responsive to the reflected light beam current signal. The signal amplifier 40 produces a reflected light beam analog voltage signal. The signal photodetector 32 can further include a signal digital voltmeter 42 which receives the reflected light beam analog voltage signal and produces a reflected light beam digital voltage signal in response thereto. The reflected light beam digital voltage signal can be input into the computer 36, which, as noted, can be a digital computer.

Similarly, reference photodetector 34 can include a reference photodiode 44 which receives the reference light beam 30 and produces the reference light beam signal as a reference light beam current signal. Reference photodetector 34 can also include a reference amplifier 46 (preferably a transresistance amplifier) which is electrically coupled to the referenced photodiode 44 and which is electrically responsive to the reference light beam current signal. The reference amplifier 46 produces a reference light beam analog voltage signal. Reference photodetector 34 can also include a reference digital voltmeter 48 which receives the reference light beam analog voltage signal and produces a reference light beam digital voltage signal in response thereto. The reference light beam digital voltage signal can be input into the computer 36 which, as noted, can be a digital computer. As noted, computer 36 can determine the temperature of the liquid based on a temperature change $\Delta T$ from a known initial temperature value. The temperature change $\Delta T$ can be determined using the formula (4) set forth above. The initial temperature value can be determined in any convenient fashion, for example, by separate measurements with a contact-type device; by initial equilibration at a known ambient temperature; or by calibration with a specimen of known temperature. In the latter case, a specimen of known temperature can be placed in the apparatus and then the actual specimen can be placed therein shortly thereafter, with the temperature change between the specimens detected. Careful control of geometry is advisable with this type of calibration.

It should be understood that the various details regarding the signal photodetector 32, reference photodetector 34, and computer 36 are merely exemplary; there are a number of different systems and techniques which can be used to generate and process signals corresponding to the intensities of the light beams 20, 22, 30. For example, calculations could be performed manually based on a readout of the voltmeters; analog voltmeters could be employed; different types of amplifiers could be employed and current rather than voltage could be sensed. Further, when digital voltmeters are referred to herein, the term should be broadly interpreted to include circuitry which converts an analog voltage signal to a digital voltage signal, with or without a readout, and it is to be understood that voltage could be read directly from the voltmeters (followed by manual calculations) or, alternatively, the voltmeters might have no visual readouts and could supply the signals directly to the computer 36. A fast digital oscilloscope can also be employed for voltage readings, to enhance response time, as discussed below in Example 5. The preferred embodiment employing transresistance amplifiers and digital voltmeters affords advantages over prior out devices using lock-in amplifiers including lower cost, greater, accuracy, and easier system operation. A "chopper" need not necessarily be used in the present invention, which is advantageous.

The foregoing discussions regarding conversion of the laser intensities to electrical signals are provided since a straightforward technique does not appear to exist at the present time to subtract the reference intensity from the signal intensity in the optical domain to obtain the change in intensity with changes in surface temperature or concentration. With the apparatus described above, the signal voltage $\Delta V$ that carries the temperature or concentration information is superimposed on a large DC voltage which results from the nominal reflected intensity. To maximize the signal to noise ratio of the system, it is desirable to enhance the percent change in the reflected signal voltage with respect to temperature or concentration, as set forth below.

Apparatus 10 can also include a first mirror 50 which directs the measurement light beam 20 onto the surface 12 of the liquid specimen 14 at an angle which enhances the percent change in reflectivity of the liquid surface 12 with respect to the temperature of the liquid. As noted, such an angle, $\alpha$, will typically be small for near-normal incidence. It will be appreciated that reflected light beam 22 reflects from surface 12 of liquid 14 at an equal angle, also designated as $\alpha$. Note that, in theory, any angle of incidence $\alpha$ such that $0° < \alpha < 90°$ will work. In practice, larger angles reduce the signal-to-noise ratio so that the aforementioned small values of $\alpha$ are preferred. Further comments regarding the angle of incidence, $\alpha$, will be set forth below.

A second mirror 52 can be provided to direct reflected light beam 22 into signal photodetector 32, for example, into signal photodiode 38.

Apparatus 10 can also include a correlator (not separately labeled) which determines the effective initial value of the reflected light beam digital voltage signal based on the reference light beam digital voltage signal and a pair of constants determined from a linear regression for a data set comprising prior values of the reference light beam digital voltage signal and prior values of the reflected light beam digital voltage signal. The prior values of both of the signals can be evaluated in a substantially unperturbed state.

The above-mentioned correlator can be, for example, a software program contained in computer 36. Appendix A (Microfiche Appendix) provides source code listing for a suitable Visual Basic program. Correlation is desirable because the beam intensities, sensitivities, and amplifier gains for the signal photodiode 38 and reference photodiode 44 are not, in general, identical. The correlator accounts for these differences. A number of measurements, N, which can be, for example, 10–50, of both the signal and reference voltages from the photodiodes 38, 44 is collected. These measurements should preferably be taken when the liquid specimen 14 is in a substantially unperturbed state (i.e., no substantial changes in temperature or concentration). A relationship between the signal and reference voltages is obtained, for example, by performing a least-squares fit (linear regression) on the resulting data set in order to determine a pair of constants a and b such that:

$$\sum_{j=1}^{N} (V_{sig,j} - (aV_{ref,j} + b))^2 \quad (5)$$

was minimized, where:

$V_{sig,j}$=signal photodiode voltage for measurement j, $V_{ref,j}$=reference photodiode voltage for measurement j.

Thus, in performing actual measurements, the constants a and b and the actual measured reference photodiode voltage are used to obtain a corresponding reading for the signal photodiode voltage, as if the liquid specimen 14 had not undergone any change. The voltage difference due to a temperature change in the liquid is then determined from the equation:

$$\Delta V = V_{sig} - (aV_{ref} + b) \tag{6}$$

where $V_{sig}$ and $V_{ref}$ are the actual values of signal and reference photodiode voltages during the measurement. Accordingly, it will be appreciated that the value for $\Delta V$ represents a difference between the signal voltage when the temperature change has occurred and a predicted value for what the signal voltage would be had there been no temperature change (determined from $V_{ref}$, a and b). It should also be noted that, although the correlator has been described with reference to operations on digital voltage signals, similar operations could be performed using analog voltage signals or using other types of signals which are indicative of the intensities of the relevant beams of light. In any event, with the system described herein, the laser beam intensity, sensitivity, and amplifier gains for the signal and reference photodiodes will not, in general, be identical and thus, the aforementioned correlation is beneficial.

Figure 2:
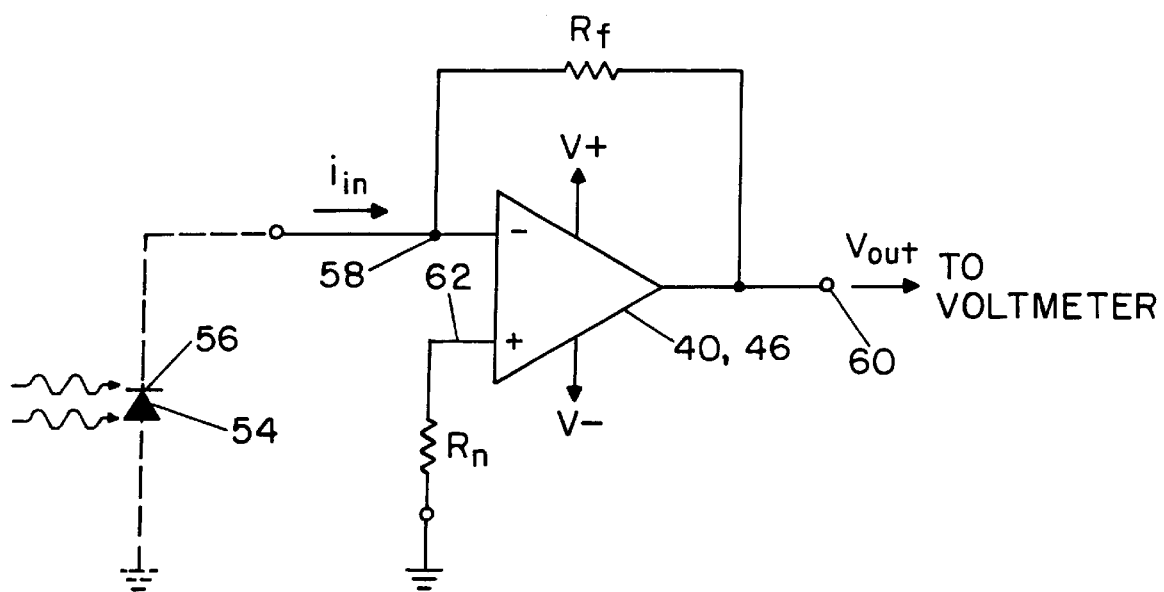
FIG. 2 is a detailed circuit diagram showing a photodiode transresistance amplifier circuit suitable for use in a detector of the present invention.

Reference should now be had to FIG. 2 which depicts exemplary details for the signal transresistance amplifier 40 and the reference transresistance amplifier 46. The same circuit can be applied to both amplifiers; in fact, the signal and reference amplifiers can be implemented in two separate channels of a multi-channel operational amplifier. The anode 54 of signal or reference photodiode 38, 44 can be grounded with the cathode 56 coupled to inverting input 58 of signal or reference transresistance amplifier 40, 46. Output 60 of the amplifier can be coupled to voltmeter 42 or 48, respectively. A feedback resistor $R_f$ can be connected between inverting input 58 and output 60, while a suitable resistor $R_n$ can be connected between the non-inverting input 62 and ground. Power can be supplied to amplifiers 40, 46 through terminals V+ and V− using known techniques, such as, for example, 9 volt batteries.

The amplifiers 40, 46 can be constructed, for example, from an Analog Devices OP-227EY low-noise, low-voltage offset, 2-channel operational amplifier. The separate channels A and B can be used for the signal and reference amplifiers 40, 46. Resistors $R_f$ and $R_n$ can be implemented with low-noise, metal film resistors with a tolerance on the order of 1.0%. They can have, for example, a value of 150 kΩ. An experimental circuit was constructed in an aluminum housing using BNC connectors, and with the indicated resistor values, attained a transresistance of $1.5 \times 10^5$ Ω, that is, the output voltage $V_{out}$ (in volts) was $1.5 \times 10^5$ times the value of the input current $i_{in}$ (in amperes). The signal to noise ratios for the circuits employed were on the order of 90–95 dB. It should be understood that any suitable amplifier circuitry can be employed; the foregoing is merely exemplary. For example, in production apparatus, a suitable circuit card containing one or more integrated circuits and/or discrete components could be employed. It is believed desirable that amplifiers 40, 46 be multiple channels in an integrated circuit device to enhance uniformity. Moreover, the photodiodes may provide a voltage output signal which may be supplied to the operational amplifier with appropriate modifications to the interconnections as will be known to those skilled in the art.

Reference should again be had to FIG. 1. The apparatus 10 depicted in FIG. 1 can also be used to measure concentration. In that case, liquid specimen 14 will of course be a multi-component liquid, since concentration measurement would otherwise be meaningless, and should be measured in a substantially isothermal condition to minimize any influence of temperature variation on the measurement. This consideration has been discussed briefly above and will be discussed in further detail below. Again, measurement light beam 20 should impinge on liquid surface 14 at a near-normal angle of incidence α. When apparatus 10 is used for concentration measurement, detector 24 determines the concentration of the liquid specimen 14 according to the formula:

$$\Delta R = (dR/dn)(\partial n/\partial C)\Delta C \tag{7}$$

where:
  $\Delta R$ is a change in the reflectivity of the liquid from a reference state as determined from the reflected light beam intensity and the measurement light beam intensity,
  n is the index of refraction of the liquid,
  dR/dn is the first derivative of the reflectivity with respect to n,
  C is the concentration of the liquid system expressed on a dimensionless volume or mass basis (i.e., volume or mass of component/total volume or mass of solution),
  $\partial n/\partial C$ is the first partial derivative of n with respect to the concentration (expressed consistently with C),
  $\Delta C$ is a change in the concentration of the liquid from a known initial value,
  $R = ((n-1)/(n+1))^2$, and (8)
  $dR/dn = 4(n-1)/(n+1)^3$. (9)

The foregoing details regarding the detector 24, including the signal photodetector 32 and reference photodetector 34, as well as the computer 36, are also applicable to concentration measurement. In concentration measurement, the computer 36 can determine the concentration of the liquid specimen based on the index of refraction of the liquid 14, the first partial derivative of the index of refraction with respect to the concentration of the liquid 14, the reflected light beam signal, and a change of the reflected light beam intensity due to a change in the concentration of the liquid 14. The change of the reflected light beam intensity can be determined using both the reference light beam signal and the reflected light beam signal.

The signal photodetector 32 can include the signal photodiode 38, signal transresistance amplifier 40, and signal digital voltmeter 42 as set forth above in the temperature measurement. Similarly, the reference photodetector 34 can include the reference photodiode 44, reference transresistance amplifier 46, and reference digital voltmeter 48 as set forth above in the temperature measurement. In concentration measurement, the computer 36, which can, as noted, be a digital computer, determines the concentration of the liquid based on a concentration change $\Delta C$ from an initial concentration value. The initial value may be, for example, known in an industrial process which starts with a pure liquid; by an initial immersion type measurement, or by calibration with a sample of known concentration (in a manner similar to that described above for temperature measurement but with $\Delta C$ rather than $\Delta T$ measured). When determining temperature or concentration with the present invention, the system can be allowed to reach equilibrium at a known, reference temperature or at a known, reference concentration with a corresponding reference reflectivity from the liquid surface.

The concentration change ΔC (on a dimensionless, volume or mass basis) can be determined using the formula:

$$\Delta C = ((n^2-1)(\Delta V))/(4(\partial n/\partial C)V_{sig}) \quad (10)$$

where:

n is the index of refraction of the liquid,

∂n/∂C is the first partial derivative of the index of refraction with respect to the concentration of the liquid (dimensionless), $V_{sig}$ is the reflected light beam digital voltage signal, and ΔV is the difference between the reflected light beam digital voltage signal and an effective initial value of the reflected light beam digital voltage signal determined using the reference light beam digital voltage signal.

First and second mirrors 50, 52 can also be employed in concentration measurement. In this case, the angle α is selected to enhance the percent change in reflectivity of the surface 12 of the liquid 14 with respect to the concentration of the liquid 14. Again, near-normal incidence is desirable, but virtually any angle will, in theory, work. Both R and dR/dn increase with the angle of incidence α of the laser beam. (Refer to F. A. Jenkins & H. E. White, *Fundamentals of Optics*(McGraw-Hill, 4th Ed. 1976)). An analysis of the ratio ΔR/R as a function of α results in a maximum at normal incidence (α=0) for both s- and p-polarized light, which explains the near-normal beam arrangement which has been found desirable in the present invention. The above discussion of α with respect to temperature measurement is also applicable here. Further comments regarding the angle of incidence, α, will be set forth below.

The aforementioned correlator can also be employed in concentration measurement. The correlating measurements will be taken at substantially constant temperature and substantially constant concentration, and the linear regression will be performed again using Equation (5) above. Equation (6) for ΔV will also be employed but will now represent a concentration change instead of a temperature change. That is, $V_{sig}$ will be the signal photodiode voltage during the actual concentration measurement and the quantity ($aV_{ref}+b$) will be the predicted value of the signal photodiode voltage, based on the reference photodiode voltage, as if no concentration change had occurred.

As shown in FIG. 1, apparatus 10, can, if desired, include a thermal control system designated generally as 62. System 62 can include, for example, a heat exchanger shell 64 which surrounds container 16 and which includes inlet and outlet ports 66, 68, respectively, which are in turn coupled to a source of heat transfer fluid 70. The source of heat transfer fluid 70 could include, for example, a heater or chiller, a pump, accumulator, and other such devices as are known in the art of thermal control. Thermal control system 62 can be used to control the temperature of liquid specimen 14 in container 16. Thermal control system 62 can be used to stabilize liquid specimen 14 at a desired reference temperature for performing initial calibration of the system. Furthermore, for experimental purposes, thermal control system 62 can be used to deliberately change the temperature of liquid specimen 14 when experiments are to be performed to compare the readings obtained by the present apparatus 10 with traditional measurement techniques.

When concentration measurements are being performed, thermal control system 62 can be used to ensure that liquid specimen 14 is kept at a substantially constant temperature, in order to minimize any extraneous changes in the reflectivity of surface 12 of liquid 14 due to temperature change.

A conventional temperature measurement device 72, such as a thermocouple or thermistor, can be provided to independently measure the temperature of liquid specimen 14 and can be connected, for example, to an additional digital voltmeter 74 which can be coupled to provide a digital representation of the liquid temperature to computer 36. Thermocouple or thermistor 72 would not normally be employed when using the apparatus in an industrial setting, since it would be contrary to the non-invasive nature of the present invention. However, its use is desirable for test and calibration purposes, in order to provide a basis for comparison with measurements taken with apparatus 10.

Note that, although container 16 and thermal control system 62 have been depicted in a form for a stagnant or quiescent liquid specimen 14, apparatus 10 can be used for surface measurements on any type of a liquid specimen which presents a suitable surface for measurement; for example, in free surface (open channel) flow.

A method of non-contact measurement of either temperature or concentration at a surface of a liquid specimen, according to the present invention, will now be described with continued reference to FIGS. 1 and 2. The method includes the step of causing a measurement light beam 20 having a measurement light beam intensity to impinge on the surface 12 of a liquid specimen 14 and to reflect back from the surface 12 as a reflected light beam 22. The reflected light beam 22 has a reflected light beam intensity which is related to both the reflectivity, R, of the liquid surface 12 and to the intensity of the measurement light beam 20. The method further includes the step of detecting the reflected light beam 22 and measuring the intensity of the reflected light beam 22; as well as the step of determining either the temperature or the concentration of the liquid specimen 14 based on the intensity of the reflected light beam 22. The method can include the additional step of providing a coherent light source; for example, light source 18 can be a laser 26. In this case, measurement light beam 20 is coherent and emanates from the coherent light source, such as laser 26.

The method can include the additional step of splitting a reference light beam 30 out of the measurement light beam 20 before the measurement light beam 20 impinges on the surface 12 of the liquid specimen 14. The reference light beam 30 has a reference light beam intensity which is indicative of the intensity of the measurement light beam 20, as discussed above with respect to the apparatus. The method can include the additional step of detecting the reference light beam 30 and measuring its intensity and then using the reference light beam intensity to compensate for intensity fluctuations in the light source 18 when determining either the temperature or the concentration of the liquid specimen 14.

When using the method of the present invention to measure temperature, the liquid specimen 14 should be either a single component liquid or a multi-component liquid with a substantially constant concentration. As for the apparatus, in the method step of causing the measurement light beam 20 to impinge on the surface 12, the measurement light beam 20 can advantageously be caused to impinge on the surface 12 at a near-normal angle of incidence α. The step of determining the temperature can include determining the temperature according to the formula (1) set forth above with respect to the apparatus. The step of detecting the reflected light beam 22 can include receiving the reflected light beam 22 in signal photodetector 32 which in turn produces a reflected light beam signal in response to the intensity of the reflected light beam. The step of detecting the reference light beam 30 can include receiving the reference light beam 30 in a reference photodetector 34 which produces a reference light beam signal in response to the intensity of the reference light beam.

The method can include the additional step of providing a computer 36 which receives digital values representative of the reflected light beam signal and the reference light beam signal, respectively, and which performs the step of determining the temperature of the liquid specimen based on the reflected light beam intensity as well as the step of using the reference light beam intensity to compensate for intensity fluctuations in the light source 18. The computer can then determine the temperature of the liquid specimen 14 based on index of refraction of the liquid 14, first derivative of the index of refraction with respect to the temperature of the liquid 14, the reflected light beam signal, and a change of the reflected light beam intensity due to a change in the temperature of the liquid 14. The change in the reflected light beam intensity can be determined using the reference light beam signal and the reflected light beam signal.

The method step of detecting the reflected light beam 30 and measuring its intensity can include providing the signal photodetector 32 as a signal photodetector assembly which includes signal photodiode 38, signal amplifier 40 (preferably a transresistance amplifier), and signal digital voltmeter 42 as discussed above. Similarly, the step of detecting the reference light beam 30 and measuring its intensity can include providing the reference photodetector 34 as a reference photodetector assembly comprising the reference photodiode 44, the reference amplifier 46 (preferably a transresistance amplifier), and the reference digital voltmeter 48, again, as set forth above with respect to the apparatus. Yet further, the step of providing the computer 36 can comprise providing a digital computer which determines the temperature of the liquid 14 based on a temperature change $\Delta T$ from an initial temperature value. The temperature change $\Delta T$ can be determined using Equation (4) as set forth above with respect to the apparatus. The initial temperature can be determined as set forth above.

The method step of causing the measurement light beam to impinge on the surface of the liquid specimen 14 can include causing the measurement light beam 20 to impinge on the surface 12 of the liquid specimen 14 at an angle, $\Delta$, which enhances the percent change in reflectivity of the liquid surface 12 with respect to the temperature of the liquid 14. As noted, this can preferably be a near-normal angle of incidence. The method can further include the additional steps of directing the reflected light beam 22 into the signal photodiode 38, such as, for example, with second mirror 52. The method can include the additional step of determining the effective initial value of the reflected light beam digital voltage signal based on the reference light beam digital voltage signal and a pair of constants determined from a linear regression, as set forth above with respect to the apparatus. As noted, the constants should preferably be evaluated from a data set which is gathered when the liquid specimen 14 is in a substantially unperturbed state (i.e., no substantial changes in temperature or concentration).

When the method of the present invention is used for concentration measurement, liquid specimen 14 is a multi-component liquid preferably maintained in a substantially isothermal condition. In the step of causing the measurement light beam 20 to impinge on the surface 12 of the liquid specimen 14, the measurement light beam 20 can be caused to impinge on the surface 12 at a near-normal angle of incidence $\alpha$, just as in the apparatus and as in the description of the method for temperature measurement. The step of determining the concentration of the liquid specimen based on the reflected light beam intensity can include determining the concentration according to the Equation (7) for $\Delta R$ as set forth above. The initial value of the concentration can also be determined as set forth above.

The steps of receiving the reflected light beam 22 in the signal photodetector 32 and receiving the reference light beam 30 in the reference photodetector 34 can be carried out in the same fashion as for temperature measurement. When it is desired to measure concentration, the method can include the additional step of providing a computer 36 which receives the reflected light beam signal (digitized for a digital computer) and the reference light beam signal (also digitized for a digital computer) and which performs the method steps of determining the concentration of the liquid specimen and using the reference light beam intensity to compensate for intensity fluctuations in the light source 18. This can in turn result in determining the concentration of the liquid specimen 14 based on the index of refraction of the liquid 14, the first partial derivative of the index of refraction with respect to the concentration of the liquid 14, the reflected light beam signal, and a change of the reflected light beam intensity due to a change in the concentration of the liquid specimen 14, with the change of the reflected light beam intensity being determined using the reference light beam signal and the reflected light beam signal.

Just as for the method for temperature measurement, the step of detecting the reflected light beam 22 can include providing the signal photodetector 32 as a signal photodetector assembly including the signal photodiode 38, signal amplifier 40 (preferably a transresistance amplifier), and signal digital voltmeter 42 as set forth above. Similarly, in the concentration measurement method, the step of detecting the reference light beam 22 can include providing the reference photodetector 34 as a reference photodetector assembly including the reference photodiode 44, reference amplifier 46 (preferably a transresistance amplifier), and reference digital voltmeter 48. Also as in the temperature measurement method, in the concentration measurement method, the step of providing the computer 36 can include providing a digital computer. The computer 36 can determine the concentration of the liquid specimen 14 based on a concentration change $\Delta C$ from an initial concentration value, with the concentration change $\Delta C$ being determined using the Equation (10) set forth above.

In the concentration measurement method, the method step of causing the measurement light beam 20 to impinge on the surface 12 of the liquid specimen 14 can include causing the measurement light beam 20 to impinge on the surface 12 at an angle, $\alpha$, which enhances the percent change in reflectivity of the liquid surface 12 with respect to the concentration of the liquid 14; again, this is preferably at a near-normal angle of incidence. Additional method steps can include directing the reflected light beam 22 into the signal photodiode 38, and determining the effective initial value of the reflected light beam digital voltage signal based on the reference light beam digital voltage signal and a pair of constants determined from a linear regression, as set forth above with respect to the apparatus.

Certain additional details will now be presented regarding the thermoreflectance measurements of temperature and concentration. The reflectivity R of the surface of a liquid depends on the liquid index of refraction n, which in turn depends on the liquid temperature T, and, for multi-component liquids, the concentration C of a particular component as well. As noted above, for both s- and p-polarized light, at near-normal incidence, reflectance R and the first derivative of the reflectance R with respect to the index of refraction n are given by Equations (2), (8) and (3), (9) above. In pure liquids, the index of refraction n is a function of the temperature T, that is, n=n(T). The change in n with temperature, dn/dT, determines the sensitivity of the reflectance R to temperature according to the formula:

$$\Delta R \cong \left(\frac{dR}{dn}\right)\Delta n = \left(\frac{dR}{dn}\right)\left(\frac{dn}{dt}\right)\Delta T, \tag{11}$$

where $\Delta T$ represents a small, finite temperature change at the liquid surface 12. When $\Delta T$ is small, on the order of 10° C., dn/dt can often be treated as approximately constant.

For mixtures of liquids, the index of refraction n depends on both the temperature and concentration, that is, n=n(T,C) with:

$$\Delta n \cong \frac{\partial n}{\partial T}\Delta T + \frac{\partial n}{\partial C}\Delta C. \tag{12}$$

With the foregoing, from Equation (11), $\Delta R$ can be approximated by the formula:

$$\Delta R \cong \frac{dR}{dn}\left[\frac{\partial n}{\partial T}\Delta T + \frac{dn}{dC}\Delta C\right]. \tag{13}$$

With reference to Equation (13) immediately above, it will be appreciated that, in order to successfully measure concentration changes $\Delta C$ with the present apparatus and method, temperature changes $\Delta T$ should be minimized, such that the liquid specimen 14 should preferably be substantially isothermal.

Because of the substantially linear response of the photodiodes 38, 44 (when operated is their linear regions) and of the (preferably transresistance) amplifiers 40, 46 described above, the ratio $\Delta R/R$ is equal to the ratio $\Delta V/V$, where $\Delta V$ is calculated from Equation (6) above and V is the signal voltage $V_{sig}$. Using this substitution in Equations (1) and (7) above, one obtains Equations (4) and (10) above for $\Delta T$ and $\Delta C$, respectively. If $I_0$ is the incident intensity from the laser 26, the reflected beam intensity at the signal photodiode 38 will be $RI_0$. The photodiode/amplifier system generates a voltage that varies linearly with the intensity of the radiation incident on the photodiode. The variation occurs according to the equations $V=A_rI_0R$, or $\Delta V=A_rI_0\Delta R$, where $A_r$ represents the intensity-to-voltage gain of the photodiode/amplifier system, and $\Delta R$ is a small change in the reflectivity. The photodiodes each generate a current proportional to the incident intensity. This current serves as the input to the corresponding transresistance amplifier, and a corresponding voltage is produced at the output, which is sent to the voltmeter.

As noted above, liquid specimen 14 should be substantially isothermal for concentration measurements; this criteria can be quantified as shown below:

$$\frac{\partial n}{\partial T}\Delta T \ll \frac{\partial n}{\partial C}\Delta C. \tag{14}$$

When it is desired to measure temperature changes in a multi-component liquid, the inequality is reversed in order to define what is meant by a substantially constant concentration.

The spatial resolution of the inventive apparatus and method is determined by the spot size of the measurement beam 20 on the surface 12 of the liquid specimen 14. In the examples set forth below, laser 26 had an exit beam diameter of 0.59 mm and a divergence angle of 1.35 mrad. No beam focusing was performed. It should be noted that if focusing were performed, a smaller spot size would be obtained (which can be advantageous), but at the cost of more noise. The beam path from laser 26 to liquid surface 12 was approximately 50 centimeters, resulting in a beam diameter of approximately 1.25 mm at the liquid surface 12. The spatial profile of the laser beam is Gaussian, and thus, the light intensity is higher in the center of the beam 20. If the apparatus and method of the present invention were employed in regions of large temperature and/or concentration gradients, liquid surface temperatures or concentrations near the center of the beam 20 would receive a higher weighting in the reflected signal, such as that from signal photodiode 38, due to the larger intensity. This occurs because a simple photodiode is incapable of determining spatial variations in the beam intensity. However, when temperature or concentration of the liquid surface are sufficiently uniform, such effects are not important.

EXAMPLE 1

An apparatus according to the present invention was assembled as shown in FIG. 1. The liquid container 16 was a plastic vial with a capacity of approximately 50 ml. Light source 18 was in the form of a laser 26, more specifically, a Melles-Griot 05-LHI-111 1 mW linearly polarized HeNe continuous wave laser with a wavelength $\lambda$=632.8 nm. Mirrors 50, 52 were aluminum coated. Thermal control system 62 included a heat exchanger shell 64 in the form of a water jacket with ports 66, 68 connected to a source of heat transfer fluid 70 in the form of a hot and cold water bath. Photodiodes 38, 44 were UDT PIN-6D silicon PIN photodiodes operating in a photoconductive mode with a 15.0V forward bias voltage applied across the diodes. Voltmeters 42, 48, 74 were Keithley Model 2000 digital voltmeters with 6.5 digits of accuracy. Digital voltage signals provided by the digital voltmeters 42, 48 and 74 were sent to computer 36, which was a personal computer, via a GPIB interface. Computer 36 ran Visual Basic for data acquisition. The entire system 10 was assembled on a vibration-isolated optical bench. Note that vibration isolation is desirable (although not necessary) with all embodiments of the present invention, in order to minimize noise and thus increase measurement resolution. Furthermore, simple averaging or other statistical techniques can be used to minimize noise and can be automated, if desired, using a suitable computer software program. The current produced in each of the photodiodes 38, 44 is proportional to the intensity of the incident light. Beam splitter 28 was a prism beam splitter.

Transresistance amplifiers 40, 46 were constructed from the Analog Devices operational amplifier discussed above. A conventional temperature measurement device 72, in the form of a thermistor coupled to an extra digital voltmeter 74 was employed. The thermistor had a diameter of approximately 2 mm, and was calibrated against a National Institute of Standards-traceable RTD probe using a large-volume temperature-controlled bath over a temperature range from 15–50° C. The thermistor resistance was monitored by the extra voltmeter 74 and was converted to the temperature near the liquid surface; this temperature was taken as the "true" temperature. The thermistor was biased by a constant current of about 0.1 mA supplied by the Keithley 2000 meter. In Example 1, measurements were made on pure 1-propanol. Relevant liquid properties for all of the liquids used in the examples are shown in Table 1. Water was not used in the examples because it has a relatively small value dn/dT, typically only 25 percent of that of the alcohols used in the examples.

ethanol as for the other fluids. With reference to Table 1, there does not appear to be any relationship between the optical and thermophysical properties of the fluid and the

TABLE 1

LIQUID PROPERTIES

| | OPTICAL PROPERTIES | | | | THERMOPHYSICAL PROPERTIES | | | | | | |
|---|---|---|---|---|---|---|---|---|---|---|---|
| | n | dn/dT (1/K) | R | dR/dn | BP (° C.) | k (W/m · K) | ρ (g/cm³) | $\mu$ (×10⁻³ Pa · s) | σ (N/m) | $C_p$ (J/g · K) | α (×10⁸ m²/s) |
| Ethanol | 1.358 | −3.9 · 10⁻⁴ | 0.023 | 0.109 | 78.2 | 0.169 | 0.7893 | 1.074 | 21.97 | 2.44 | 8.775 |
| Methanol | 1.325 | −3.9 · 10⁻⁴ | 0.020 | 0.103 | 64.6 | 0.200 | 0.7914 | 0.544 | 22.07 | 2.53 | 9.989 |
| Propanol | 1.384 | −3.9 · 10⁻⁴ | 0.026 | 0.113 | 97.2 | 0.154 | 0.8305 | 1.945 | 23.32 | 2.39 | 7.759 |

Figure 3A:
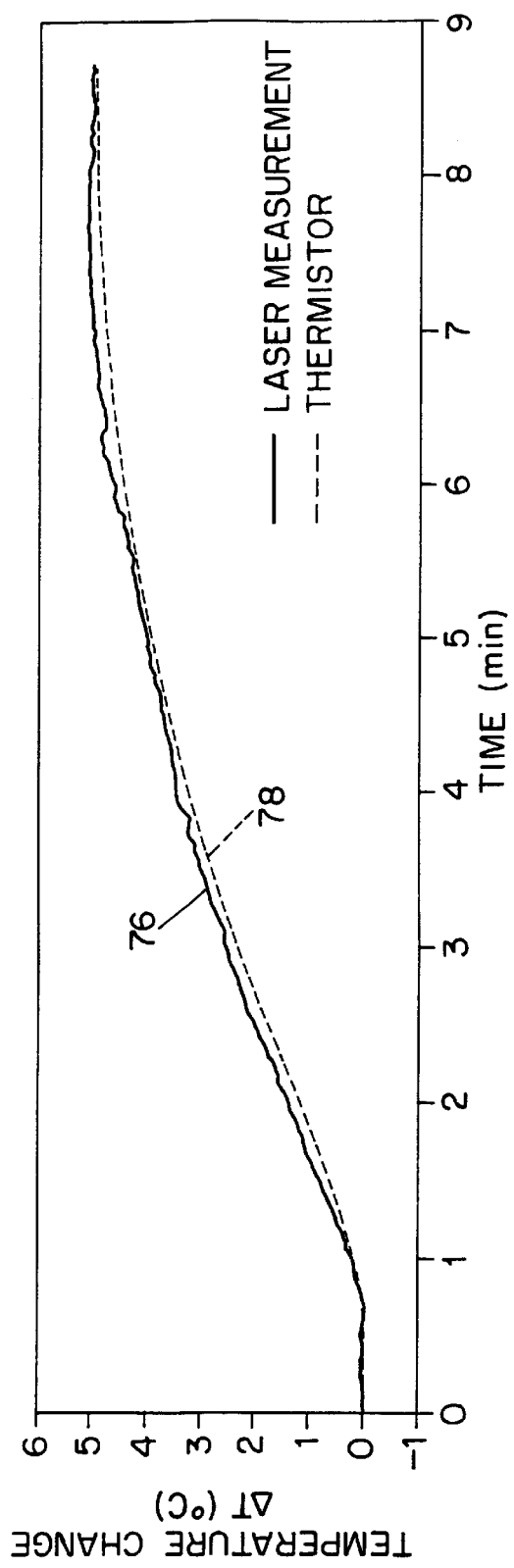
FIG. 3A depicts temperature measurement results obtained with the present invention for heating of 1-propanol compared with a thermistor measurement.
Figure 3B:
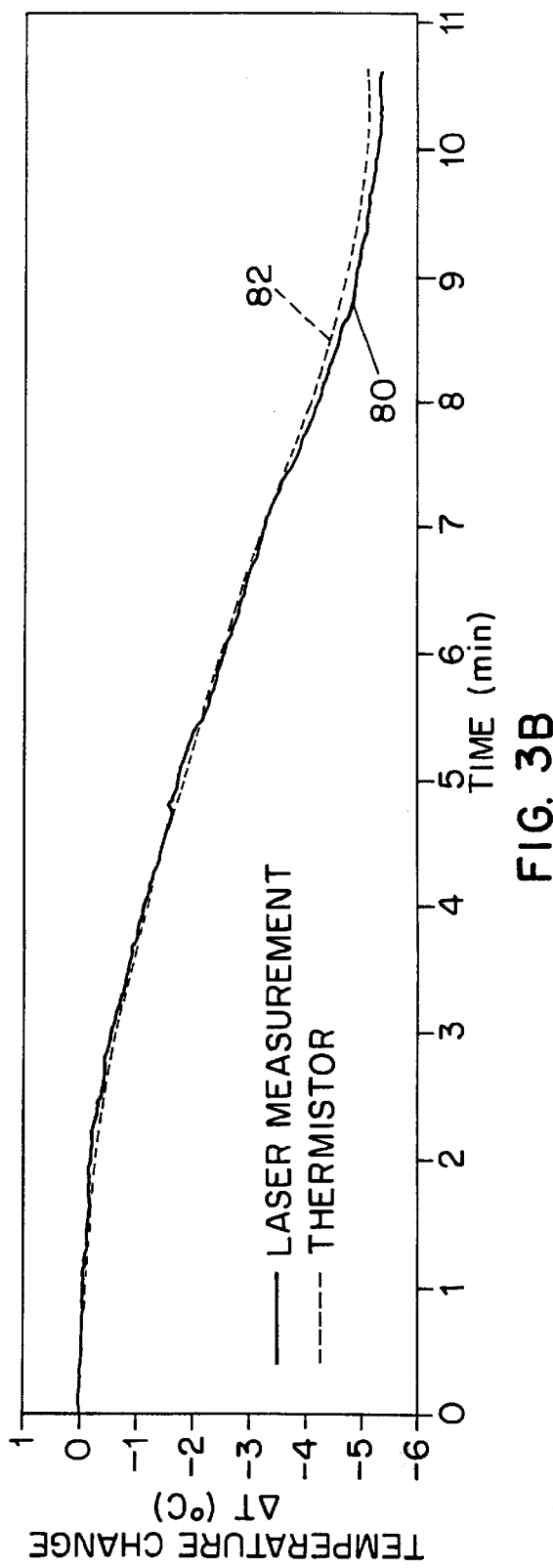
FIG. 3B is a graph similar to FIG. 3A except that the measurement is taken while the liquid is cooling.
Figure 3C:
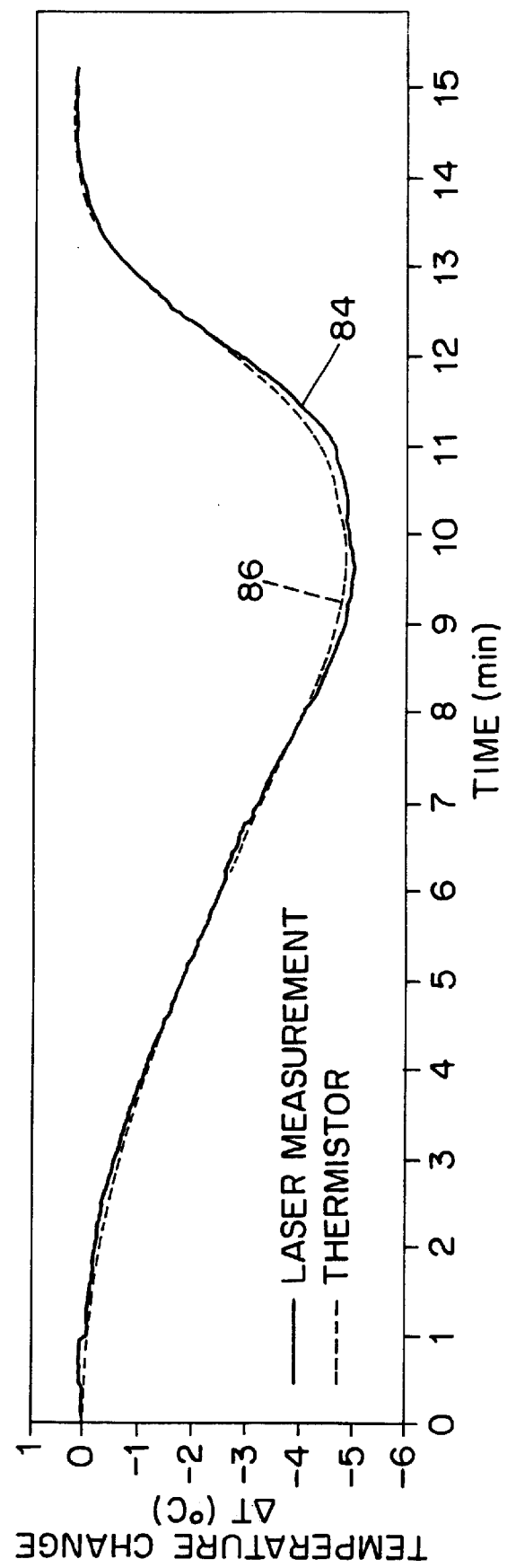
FIG. 3C is a figure similar to FIGS. 3A and 3B showing measurements taken while the liquid is first cooled, then heated.

A pure heating process was conducted and the results are shown in FIG. 3A, where the solid line 76 represents the measurement from the present method and the dashed line 78 represents the readout of the thermistor. Similar plots are shown for a cooling process in FIG. 3B and for a cooling and heating process in FIG. 3C. The solid lines 80, 84 represent measurements taken with the present invention while the dashed lines 82, 86 represent the control measurements using the thermistor. The system was allowed to stabilize thermally for at least 10–15 minutes before each test and a plastic enclosure was placed over the container 16, diodes 38, 44, and the optical surfaces, to reduce noise fluctuations. Use of the linearly polarized laser is also beneficial in reducing noise and drift. Use of a relatively large prism beam splitter for beam splitter 28 helped to avoid production of satellite beams in the vicinity of the photodiodes. Further, the experiment was run in a darkened room to avoid influence from outside room lights. As shown in FIGS. 3A, 3B and 3C, the correlation between the thermistor measurements and the measurements with the present technique is very good. Note that no adjustable parameters were employed in determination of the results for Examples 1–3 as shown in FIGS. 3–5. Equations (1), (2) and (3) were used to relate the reflectivity change to the temperature change, with values of n and dn/dT (=∂n/∂T for pure liquid) taken from the literature. D. Solimini, "Loss Measurements of Organic Materials at 6328 Å," *J. Appl. Phys.*, v.37, 3314–15 (1966).

EXAMPLE 2

Figure 4C:
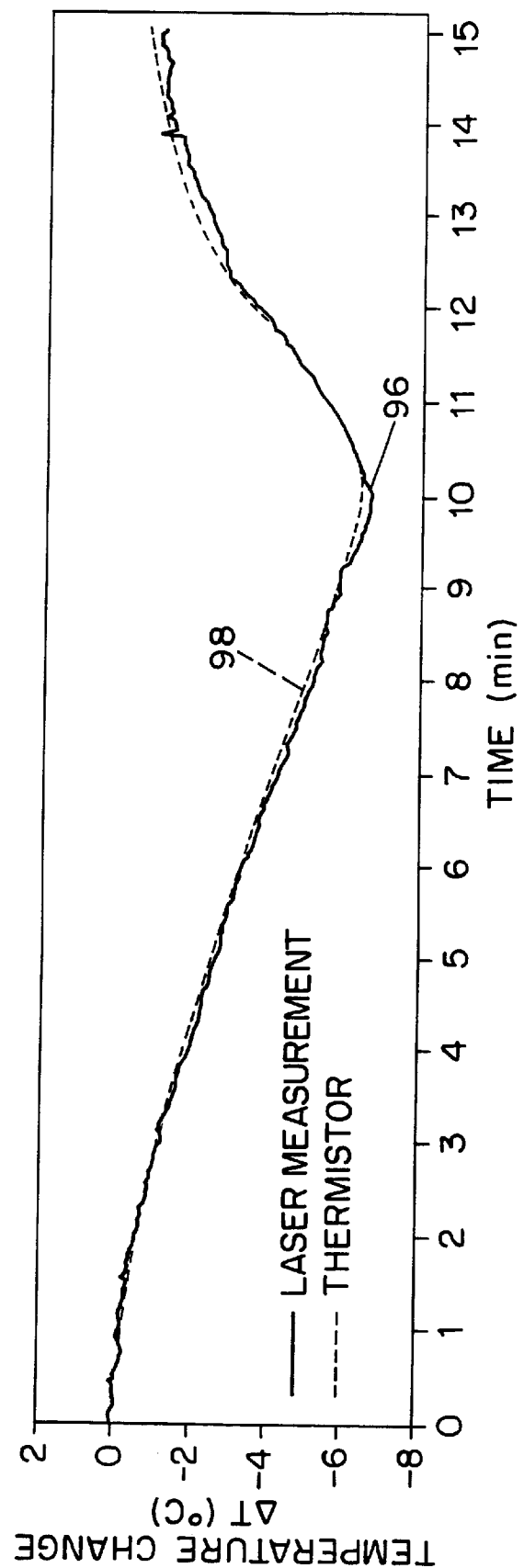
FIG. 4C is similar to FIG. 3C except that the liquid is methanol.

The experiment of Example 1 was repeated with an identical setup except that methanol was used instead of 1-propanol. FIG. 4A represents heating; FIG. 4B represents cooling; and FIG. 4C represents cooling followed by heating. The solid lines 88, 92, 96 represent the measurements of the present invention, while the dotted lines 90, 94, 98 represent the control measurements using the thermistor. Again, it is seen that the correlation is quite good, although not quite as good as that obtained in Example 1.

EXAMPLE 3

Figure 5A:
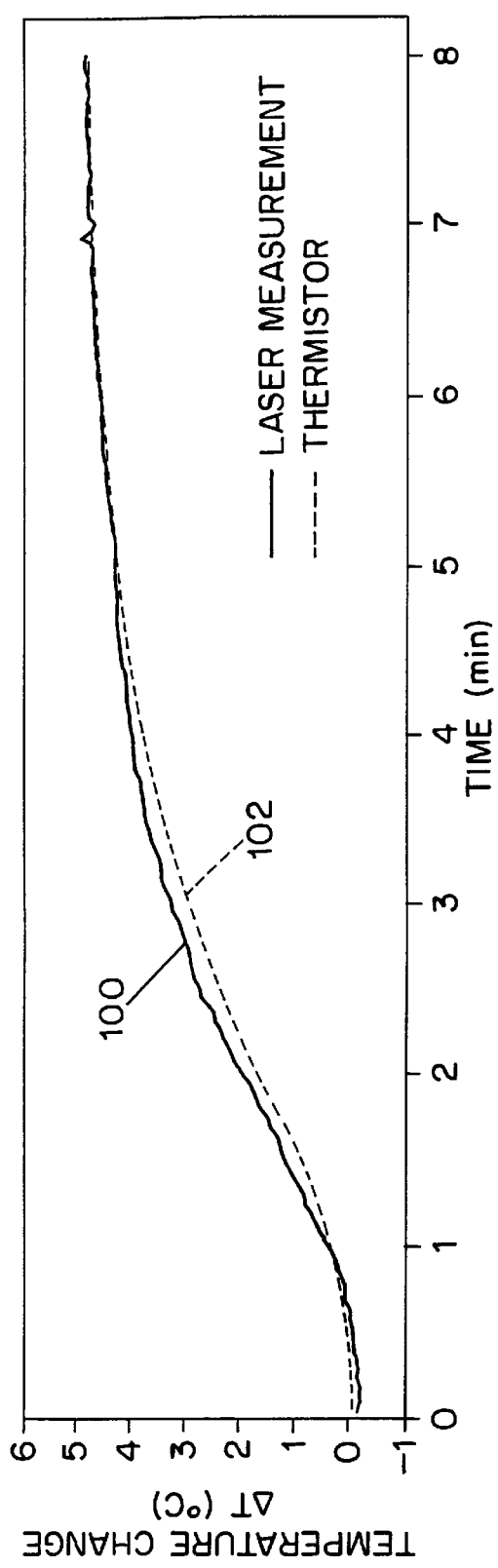
FIG. 5A is similar to FIG. 3A except that the liquid is ethanol.
Figure 5B:
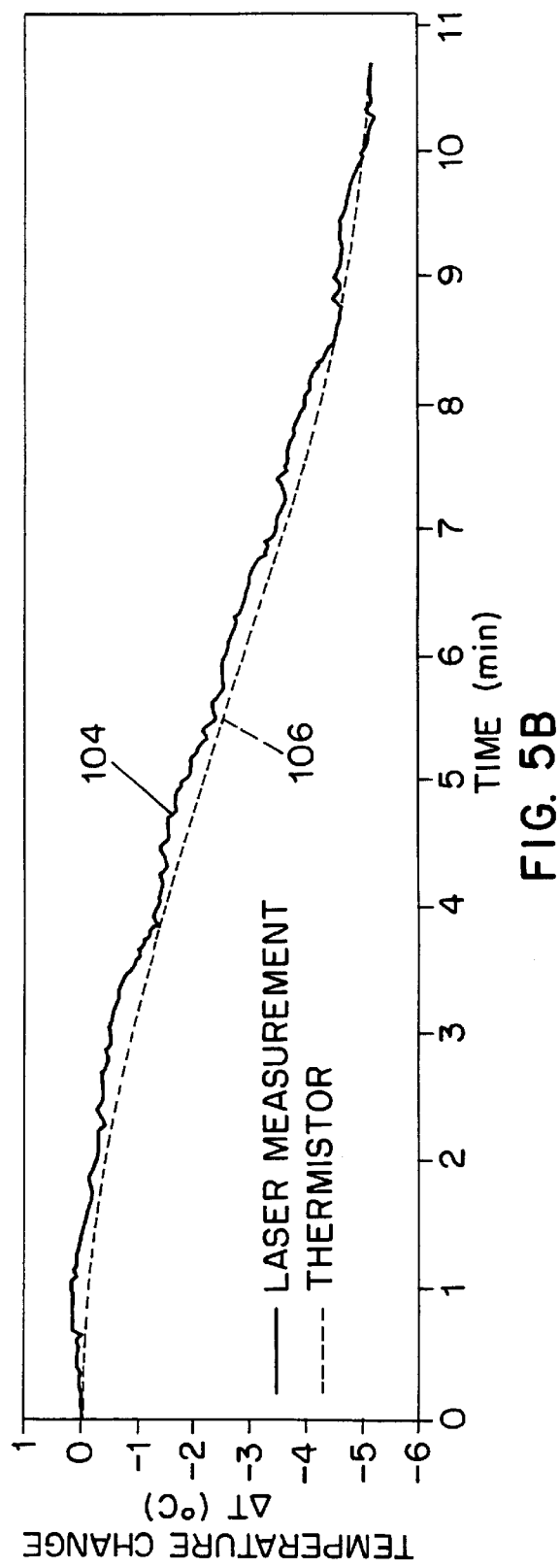
FIG. 5B is similar to FIG. 3B except that the liquid is ethanol.
Figure 5C:
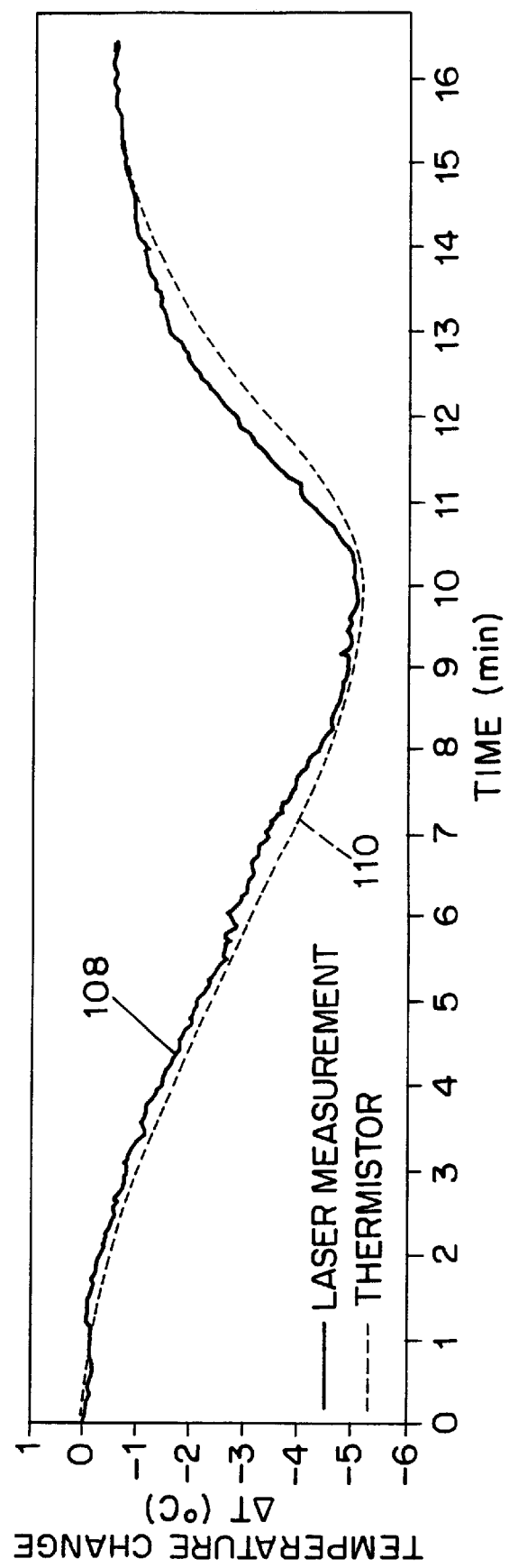
FIG. 5C is similar to FIG. 3C except that the liquid is ethanol.

The experiment of Example 1 was again repeated, for ethanol. Results for heating, for cooling, and for cooling followed by heating are shown in FIGS. 5A, 5B and 5C, respectively. The solid lines 100, 104, 108 represent the measurements in accordance with the present invention while the dashed lines 102, 106, 110 represent the control measurements using the thermistor. Correlation is again quite good, however, the correlation is not as good for success of the correlation. It is believed that environmental factors, such as building vibration, may play a role.

EXAMPLE 4

An experiment was conducted using an apparatus according to the present invention as described above. The fluid was a mixture of 1-propanol and methanol. A prior art measurement technique was used to construct a plot of the refractive index, n, as a function of the volume-based concentration of 1-propanol. Initially, 100% methanol was employed with propanol gradually added until a concentration of about 60% propanol was obtained. This corresponds to curve 112 in FIG. 6. Then, an experiment was performed with 100% propanol, with methanol gradually added until a final concentration of only about 40% propanol was obtained. This is curve 114 in FIG. 6. It can be seen that agreement in the central, overlapping region was quite good. Although this system is linear, other systems may not be, for example, an ethanol-water mixture shows a non-linear dependence of index of refraction n based on concentration.

In general, when two liquids, A and B are mixed together in different volume fractions, the volume concentrations $C_A$ and $C_B$ of liquids A and B are, respectively:

$$C_A = V_A/(V_A + V_B) \tag{15}$$

$$C_B = V_B/(V_A + V_B), \text{ and} \tag{16}$$

$$C_A + C_B = 1 \tag{17}$$

where $V_A$ and $V_B$ are the volume fractions of liquids A and B respectively.

Note that mass concentrations can be used instead of volume concentrations in any case, particularly when using solid solutes, or when mixing liquids where the resulting solution has a lower volume than do the separate components. Mass fractions $M_A$ and $M_B$ of components A & B are substituted for $V_A$ and $V_B$, respectively, in the above equation. Further, one of skill in the art can easily ascertain molar concentration knowing mass and molecular weight. Accordingly, throughout the present specification and claims, "mass concentrations" should be taken to include molar concentrations.

Figure 6:
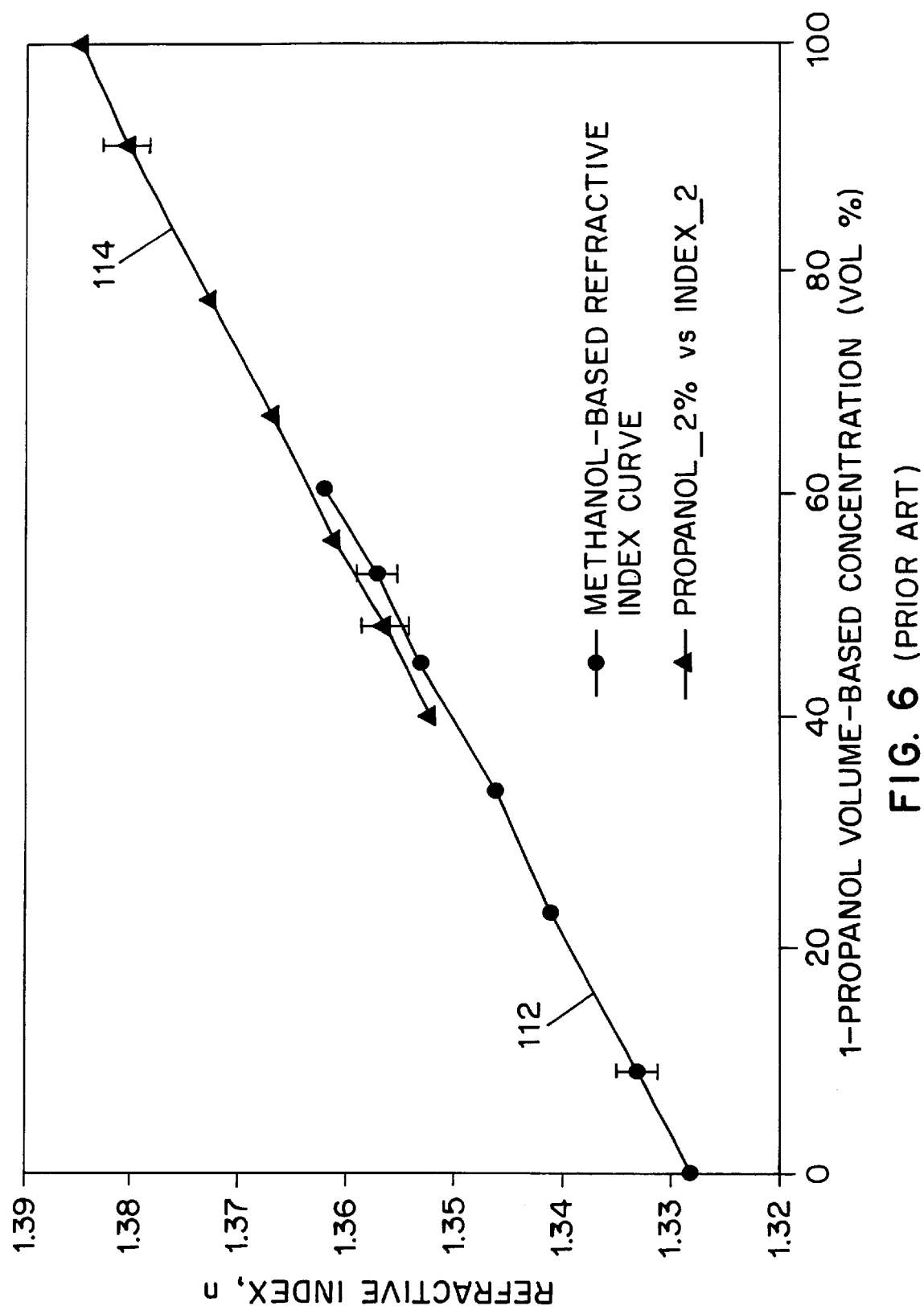
FIG. 6 depicts a graph of refractive index versus 1-propanol volume-based concentration determined using a prior art method.
Figure 7:
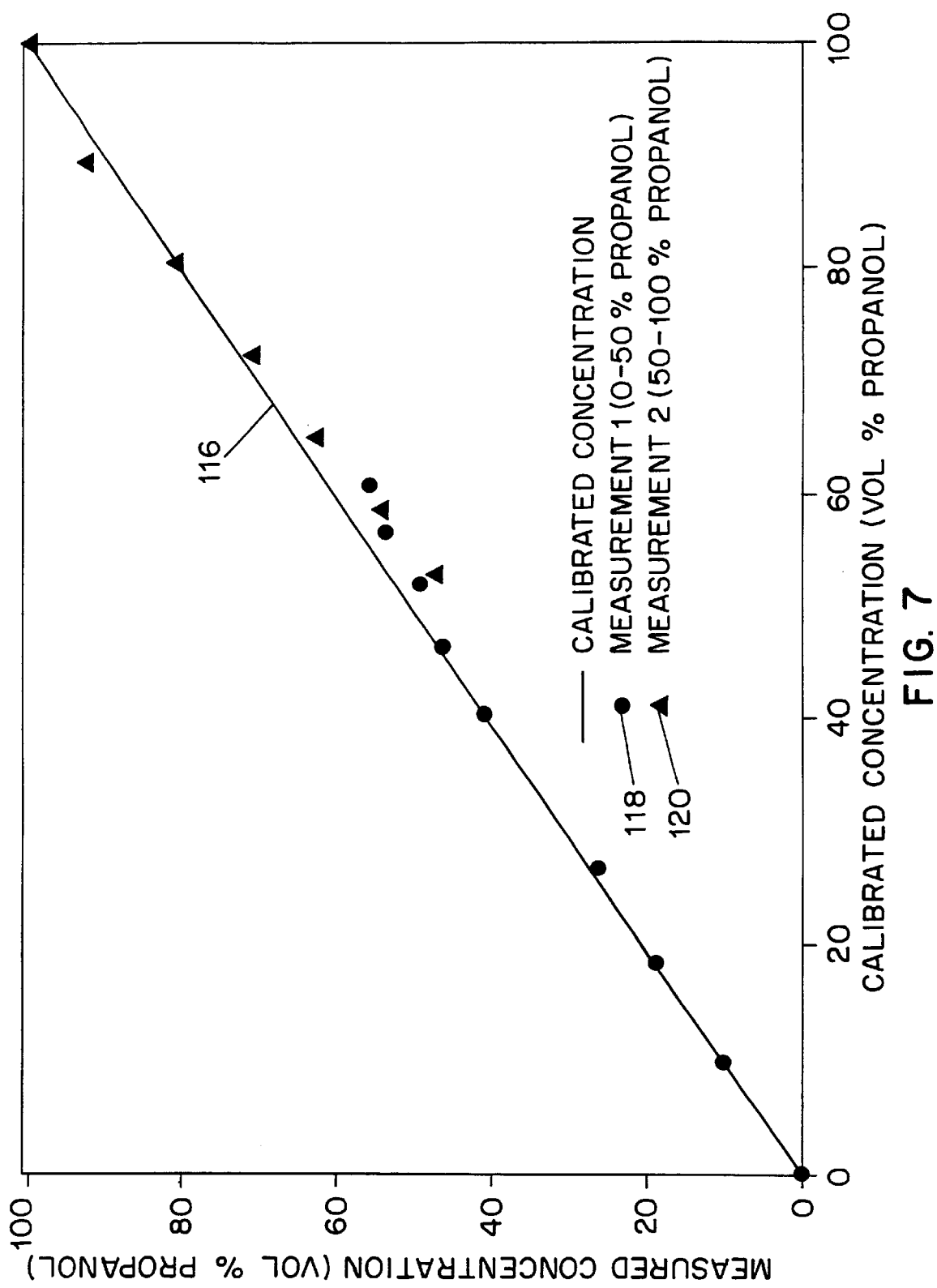
FIG. 7 depicts concentration measurement results from the present invention.

The data in FIG. 6 were used to determine a value of dn/dC=5.7+10⁻⁴ per percent change in concentration. This value was employed in Equation (10) above, with the total derivative substituting for the partial derivative at constant temperature. Results of the experiment conducted with the present invention are shown in FIG. 7. The solid line of unity slope 116 represents the ideal performance where the measured concentration is exactly equal to the calibrated concentration. The actual experimental results are indicated by the circular data points 118 and the triangular data points 120. The circular data points 118 represent a first series of measurements from 0–50% propanol, while the triangular data points 120 represent a second series of measurements from 50–100% propanol. There is some overlap in the middle. For the round data points 118, initially, a sample of 100% methanol was employed to which propanol was gradually added. Because of the large volumes of propanol required to dilute the methanol concentration to a low value, the second experiment started with 100% propanol and gradually added methanol to reduce the propanol concentration. It can be seen that the agreement is quite good; the data points near the middle of the graph show the greatest discrepancy, but this may be due to errors in the concentration caused by the cumulative addition of volumes of fluid.

EXAMPLE 5

Experiments were conducted to quantify drift in the present invention. Thermistor 72 was calibrated in a separate temperature-controlled water bath using a National Institute of Standards-traceable platinum-resistance RTD thermometer with a reported accuracy of 0.01° C. Bath temperatures ranging from 15 to 50° C. were used. Several resistance values of the thermistor and RTD were taken once the water bath stabilized. The RTD probe was taken as the true temperature and the average and standard deviation for the thermistor readings were computed. The results indicated that in the range from 15–50° C., a thermistor uncertainty of less than 0.05° C. can be expected. Liquid was metered using 1 cc hypodermic syringes, which are graduated to 0.01 cc. Typical uncertainty of delivery was ±0.01 cc. With reference to FIG. 7, since each data point represents an exchange of liquid, the uncertainty in concentration increases with increasing liquid exchanges and is equal to the number of data points multiplied by the uncertainty of each exchange. The maximum uncertainty occurs near the center, with a potential accumulated volume error of approximately 0.1 cc for ten exchanges. With a typical working volume of liquid of 10 cc, the total uncertainty in the calibrated concentration was therefore ±1%. The laser-based system exhibits a long-term drift as well as small reading-to-reading fluctuations in temperature during the measurement process, as shown in FIGS. 3–5. Despite the foregoing uncertainty analysis, neither the source of the noise, nor the factors that affect it, are apparent at this time. Interference effects in the optical path resulting from small temperature variations or small vibrations of the optical table are one possibility. In this example, the uncertainty has been characterized empirically, as described below.

The present invention is capable of operating without a lock-in amplifier, which has been used by others for thermoreflectance-based measurements, as shown in the above-mentioned papers by Qiu et al., Lee et al., and Lee and Norris. In the experiments described in the foregoing examples, the largest single source of noise has been found to be long-term drift in the system, occurring over a time frame on the order of minutes or more. Lock-in amplifiers employed in prior methods and systems are ideal for extracting signals buried in noise of a much higher relative amplitude. In the present invention, the signal-to-noise ratio is reasonable and, as noted, the largest source of errors occurs due to long-term drift. The temporal resolution of the method and apparatus of the present invention is limited by the electrical components, rather than the optical components. The photodiodes 38, 44 and the transresistance amplifiers 40, 46 have a response time of 1 $\mu s$ or less. The digital voltmeters 42, 48, 74 have a slower response time on the order of 1 ms. A fast digital oscilloscope can be used to measure the photodiode currents instead of the foregoing system, if faster response times are required. However, the aforementioned long-term drift in the system between the calibration and test times becomes significant after about 20 or 30 seconds. A small but significant, and cumulative drift in the output signal tends to be encountered even if no temperature or concentration changes occur in the liquid system. The magnitude of the signal being measured is small, and therefore, even small fluctuations in the system can lead to significant drift.

Figure 8:
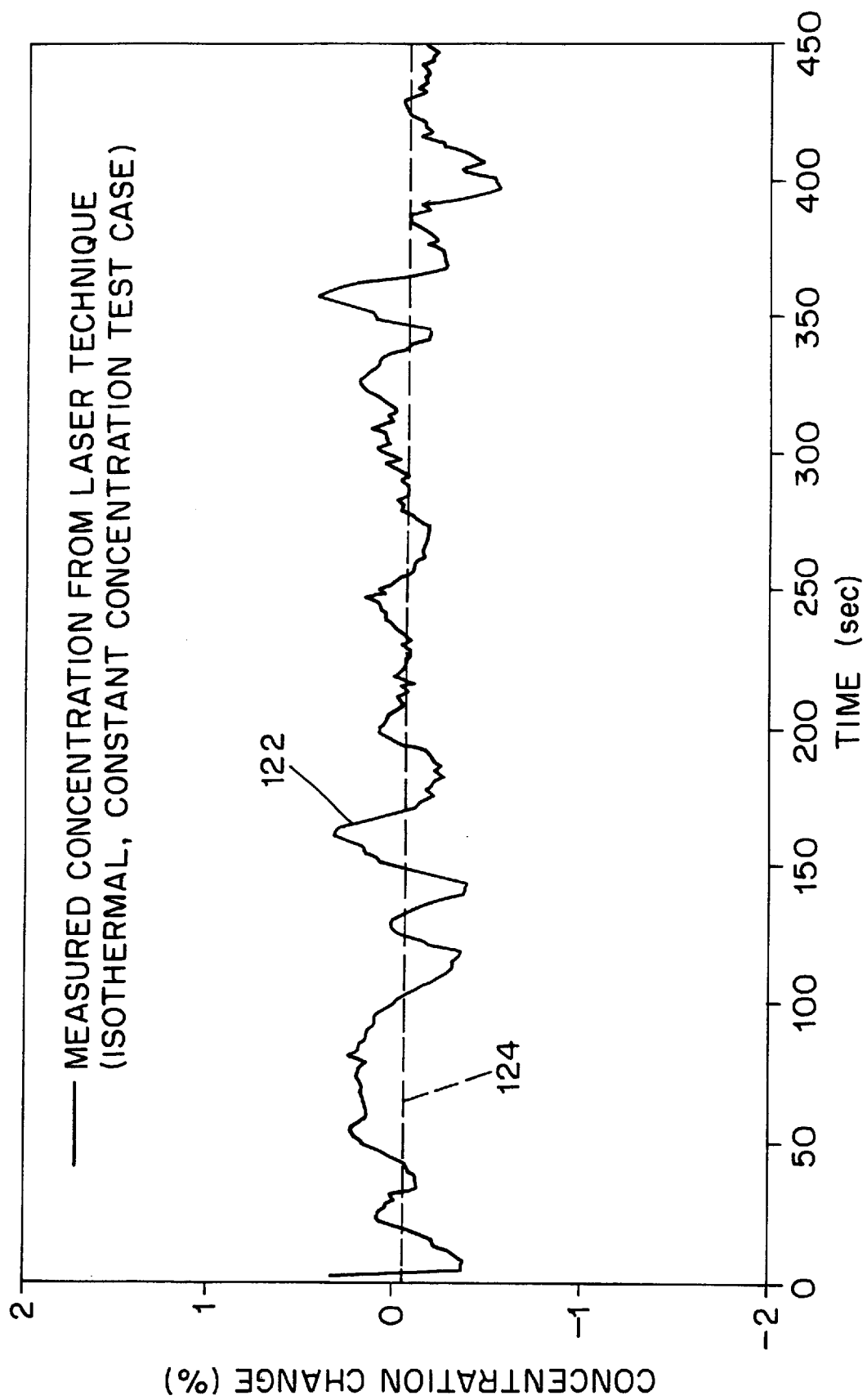
FIG. 8 depicts the result of an isothermal, constant-concentration test conducted with the present invention to quantify the influence of noise.

To quantify the drift, the system was set up for concentration measurement, and an isothermal liquid mixture of 50/50 methanol-propanol was measured. The results are shown in FIG. 8. In principle, the signal shown by the solid line 122 should remain constant, but due to the noise, there is a slight fluctuation. The mean value, indicated by the dashed line 124, remains near 0. Thus, FIG. 8 illustrates the effect of concentration change due to noise. As can be seen, the uncertainty due to this phenomena is approximately ±0.5%.

Further Comments on the Angle of Incidence

It is desired to maximize the percent change in reflectivity with index of refraction. Thus, the quantity $(1/R)(dR/dn)$ should be as large (negative) as possible. The reflectivity, R, is given by:

$$R_p(\alpha)=(\tan\ (\alpha-\phi(\alpha))/\tan\ (\alpha+\phi(\alpha)))^2 \text{for p-polarized light}, \qquad (18)$$

and by:

$$R_s(\alpha)=(\sin\ (\alpha-\phi(\alpha))/\sin\ (\alpha+\phi(\alpha)))^2 \text{ for s-polarized light}, \qquad (19)$$

where:

$$\phi(\alpha)=\text{arc sin } (\sin\ (\alpha)n_1/n_2) \qquad (20)$$

$n_1$=index of refraction of atmosphere, and
$n_2$=index of refraction of liquid.

Figure 9:
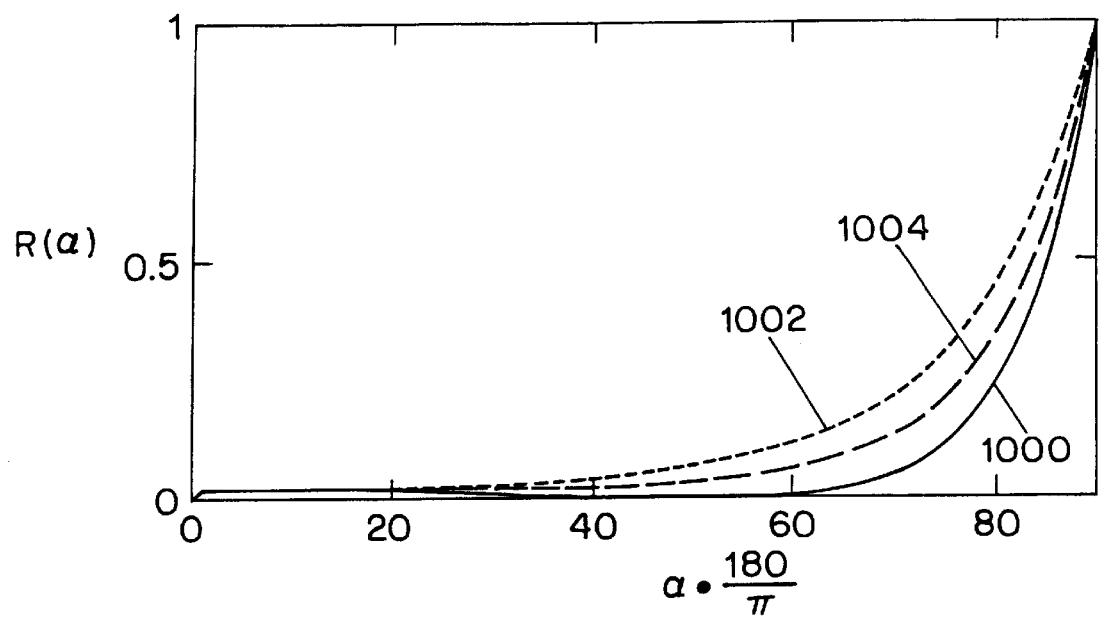
FIG. 9 is a plot of reflectivity vs. angle of incidence.
Figure 10:
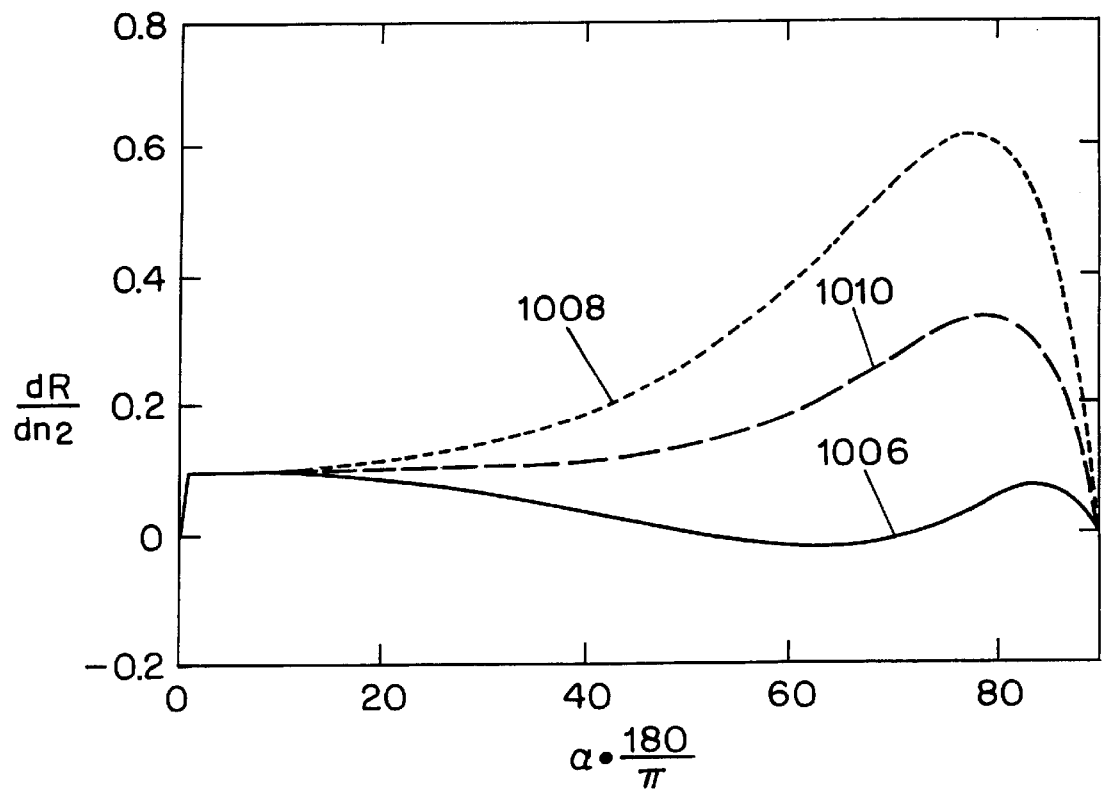
FIG. 10 is a plot of first derivative of reflectivity with respect to index of refraction vs. angle of incidence.
Figure 11:
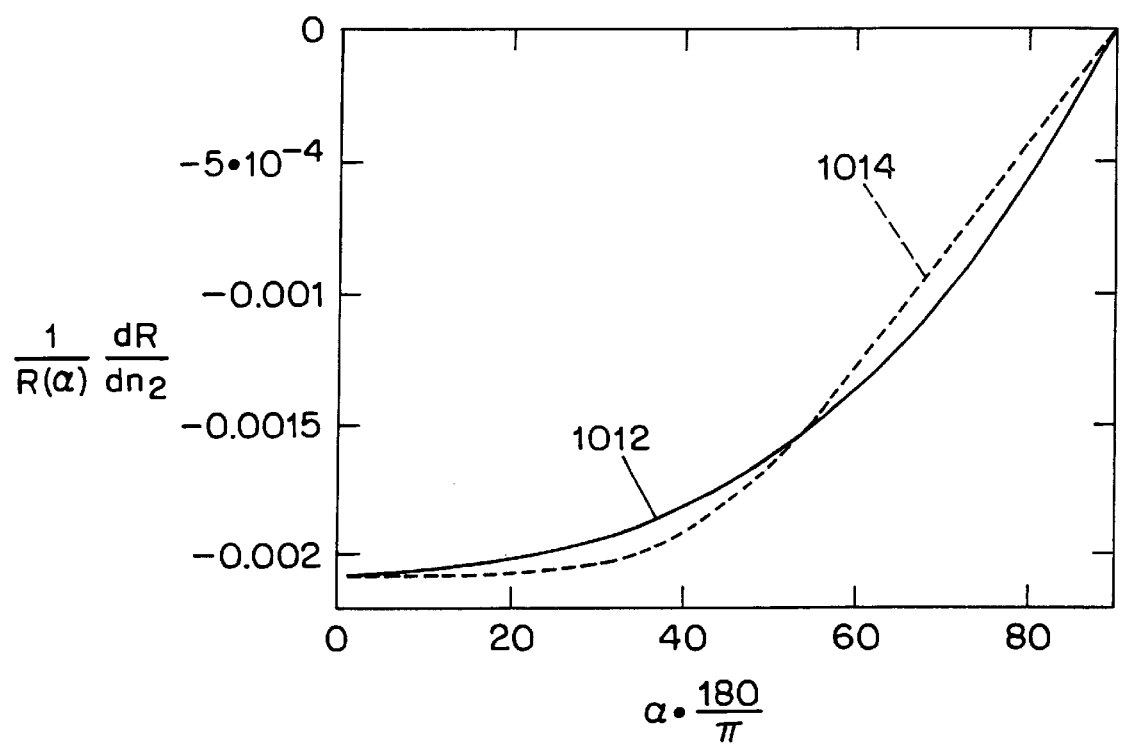
FIG. 11 is a plot of percent change of reflectivity vs. angle of incidence.

The total average reflectivity $R_t\ (\alpha)=\frac{1}{2}(R_p(\alpha)+R_s(\alpha))$. FIG. 9 shows $R_p$, $R_s$ and $R_t$ plotted vs. $\alpha$ (in degrees) as curves 1000, 1002 and 1004 respectively. FIG. 10 plots the derivatives of each of these quantities with respect to $n_2$ as curves 1006, 1008 and 1010 respectively. Finally, FIG. 11 shows $(1/R_s)(dR_s/dn_2)$ and $(1/R_t)(dR_t/dn_2)$ plotted as curves 1012, 1014 respectively. It can be seen that these quantities achieve a (negative) maximum value at $\alpha=0°$. No curve is shown for p-polarized light at present. FIGS. 9–11 are based on $n_1=1.0$, $n_2=1.331$ (nominal) and $dn/dT=-4\times10^{-4}$. Points were plotted every $\pi/200$ radians.

Although the present invention has been described with reference to specific exemplary embodiments, it should be understood that various changes, substitutions and alterations can be made to the disclosed embodiments without departing from the spirit and scope of the invention as defined by the appended claims.

What is claimed is:

1. An apparatus for non-contact measurement of concentration at a surface of a liquid specimen, said apparatus comprising:
   (a) a light beam provider which produces a measurement light beam, having a measurement light beam intensity, which impinges on the surface of the liquid specimen and reflects back as a reflected light beam with a reflected light beam intensity related to both reflectivity, R, of the liquid surface and said measurement light beam intensity;

(b) a detector which receives said reflected light beam and determines said reflected light beam intensity; and (c) means for determining the concentration of the liquid specimen from said reflected light beam intensity.

2. The apparatus of claim 1, wherein said light beam provider includes a coherent light source.

3. The apparatus of claim 2, wherein:

the liquid is a multi-component liquid maintained in a substantially isothermal condition;

said light beam provider produces a measurement light beam which impinges on the liquid surface at a near-normal angle of incidence; and said determining means determines the concentration of the liquid specimen according to the formula:

$$\Delta R = (dR/dn)(\partial n/\partial C)\Delta C$$

where:

$\Delta R$ is a change in the reflectivity of the liquid specimen from a reference state as determined from said reflected light beam intensity and said measurement light beam intensity, n is index of refraction of the liquid specimen, dR/dn is first derivative of the reflectivity with respect to n, C is the concentration of the liquid system expressed on one of a volume and a mass basis, $\partial n/\partial C$ is first partial derivative of n with respect to the concentration, expressed on a consistent basis, $\Delta C$ is a change in the concentration of the liquid from a known initial value, $R = ((n-1)/(n+1))^2$, and $dR/dn = 4(n-1)/(n+1)^3$.

4. The apparatus of claim 2, wherein said light beam provider includes a beam splitter which provides a reference light beam and passes said measurement light beam to impinge on the surface of the liquid specimen, said reference light beam having a reference light beam intensity which is indicative of said measurement light beam intensity, wherein said determining means also receives said reference light beam and also uses said reference light beam intensity to determine the concentration of the liquid specimen, said reference light beam intensity being used to compensate for fluctuations in said measurement light beam intensity.

5. The apparatus of claim 4, wherein the liquid specimen is a multi-component liquid specimen maintained in a substantially isothermal condition, and wherein said detector comprises:

(i) a signal photodetector which receives said reflected light beam and produces a reflected light beam signal indicative of the intensity of said reflected light beam; and (ii) a reference photodetector which receives said reference light beam and produces a reference light beam signal indicative of the intensity of said reference light beam; and wherein said determining means comprises:

a computer which receives said reflected light beam signal and said reference light beam signal and which determines the concentration of the liquid specimen based on:

index of refraction of the liquid, first partial derivative of the index of refraction with respect to the concentration of the liquid specimen, said reflected light beam signal, and a change of said reflected light beam intensity due to a change in the concentration of the liquid specimen, said change of said reflected light beam intensity being determined using said reference light beam signal and said reflected light beam signal.

6. The apparatus of claim 5, wherein:

said computer is a digital computer;

said signal photodetector comprises:

a signal photodiode which receives said reflected light beam and produces said reflected light beam signal;

a signal amplifier electrically coupled to said signal photodiode and electrically responsive to said reflected light beam signal, said signal amplifier producing a reflected light beam analog voltage signal; and a signal digital voltmeter which receives said reflected light beam analog voltage signal and produces a reflected light beam digital voltage signal in response thereto, said reflected light beam digital voltage signal being input to said digital computer;

said reference photodetector comprises:

a reference photodiode which receives said reference light beam and produces said reference light beam signal;

a reference amplifier electrically coupled to said reference photodiode and electrically responsive to said reference light beam signal, said reference amplifier producing a reference light beam analog voltage signal; and a reference digital voltmeter which receives said reference light beam analog voltage signal and produces a reference light beam digital voltage signal in response thereto, said reference light beam digital voltage signal being input to said digital computer; and said digital computer determines the concentration of the liquid specimen based on a concentration change $\Delta C$ from an initial concentration value, the concentration change $\Delta C$ being determined using the formula:

$$\Delta C = ((n^2-1)(\Delta V))/(4(\partial n/\partial C)V_{sig})$$

where:

n is the index of refraction of the liquid specimen, $\partial n/\partial C$ is the first partial derivative of the index of refraction with respect to the concentration of the liquid specimen, expressed on one of a mass and a volume basis, $V_{sig}$ is said reflected light beam digital voltage signal, and $\Delta V$ is a difference between said reflected light beam digital voltage signal and an effective initial value of said reflected light beam digital voltage signal determined using said reference light beam digital voltage signal.

7. The apparatus of claim 6, wherein said light beam provider includes:

a first mirror which directs said measurement light beam onto the surface of the liquid specimen at an angle which enhances percent change in reflectivity of the liquid specimen surface with respect to the concentration of the liquid specimen;

a second mirror which directs said reflected light beam into said signal photodiode; and a correlator which determines said effective initial value of said reflected light beam digital voltage signal based on:

said reference light beam digital voltage signal; and a pair of constants determined from a linear regression for a data set comprising prior values of said reference light beam digital voltage signal and prior values of said reflected light beam digital voltage signal, said prior values of both of said signals being evaluated in a substantially unperturbed state.

8. The apparatus of claim 1, further comprising a container which contains the liquid specimen.

9. A method for non-contact measurement of concentration at a surface of a liquid specimen, said method comprising the steps of:

(a) causing a measurement light beam having a measurement light beam intensity to impinge on the surface of the liquid specimen and to reflect back from the surface as a reflected light beam with a reflected light beam intensity related to both reflectivity, R, of the liquid specimen surface and said measurement light beam intensity;

(b) detecting said reflected light beam and measuring said reflected light beam intensity; and (c) determining the concentration of the liquid specimen based on said reflected light beam intensity.

10. The method of claim 9, further comprising the additional step of providing a coherent light beam as the measurement light beam.

11. The method of claim 10, wherein:

the liquid specimen is a multi-component liquid maintained in a substantially isothermal condition;

in step (a), said measurement light beam is a caused to impinge on the surface of the liquid specimen at a near-normal angle of incidence; and step (c) comprises determining the concentration of the liquid specimen according to the formula:

$$\Delta R = (dR/dn)(\partial n/\partial C)\Delta C$$

where:

$\Delta R$ is a change in the reflectivity of the liquid specimen from a reference state as determined from said reflected light beam intensity and said measurement light beam intensity, n is index of refraction of the liquid specimen, dR/dn is first derivative of the reflectivity with respect to n, C is the concentration of the liquid system expressed on one of a volume and a mass basis, $\partial n/\partial C$ is first partial derivative of n with respect to the concentration, expressed on a consistent basis, $\Delta C$ is a change in the concentration of the liquid specimen from a known initial value, $R=((n-1)/(n+1))^2$, and $dR/dn=4(n-1)/(n+1)^3$.

12. The method of claim 10, further comprising the additional steps of:

(d) splitting a light beam into a reference light beam and said measurement light beam, said reference light beam having a reference light beam intensity which is directly proportional to said measurement light beam intensity;

(e) detecting said reference light beam and measuring said reference light beam intensity; and (f) using said reference light beam intensity to compensate for fluctuations in the intensity of the measurement light beam when determining the concentration of the liquid specimen.

13. The method of claim 12, wherein:

the liquid is a multi-component liquid maintained in a substantially isothermal condition;

step (b) comprises receiving said reflected light beam in a signal photodetector which produces a reflected light beam signal indicative of the intensity of said reflected light beam; and step (e) comprises receiving said reference light beam in a reference photodetector which produces a reference light beam signal indicative of the intensity of said reference light beam;

further comprising the additional step of providing a computer which receives said reflected light beam signal and said reference light beam signal and which performs steps (c) and (f) to determine the concentration of the liquid specimen based on:

index of refraction of the liquid specimen, first partial derivative of the index of refraction with respect to the concentration of the liquid, said reflected light beam signal, and a change of said reflected light beam intensity due to a change in the concentration of the liquid specimen, said change of said reflected light beam intensity being determined using said reference light beam signal and said reflected light beam signal.

14. The method of claim 13, wherein:

step (b) comprises providing said signal photodetector as a signal photodetector assembly comprising:

a signal photodiode which receives said reflected light beam and produces said reflected light beam signal;

a signal amplifier electrically coupled to said signal photodiode and electrically responsive to said reflected light beam signal, said signal amplifier producing a reflected light beam analog voltage signal; and a signal digital voltmeter which receives said reflected light beam analog voltage signal and produces a reflected light beam digital voltage signal in response thereto, said reflected light beam digital voltage signal being input to said digital computer;

step (e) comprises providing said reference photodetector as a reference photodetector assembly comprising:

a reference photodiode which receives said reference light beam and produces said reference light beam signal;

a reference amplifier electrically coupled to said reference photodiode and electrically responsive to said reference light beam signal, said reference amplifier producing a reference light beam analog voltage signal; and a reference digital voltmeter which receives said reference light beam analog voltage signal and produces a reference light beam digital voltage signal in response thereto, said reference light beam digital voltage signal being input to said digital computer; and said step of providing said computer comprises providing a digital computer which determines the concentration of the liquid specimen based on a concentration change $\Delta C$ from an initial concentration value, the concentration change $\Delta C$ being determined using the formula:

$$\Delta C = ((n^2-1)(\Delta V))/(4(\partial n/\partial C)V_{sig})$$

where:
n is the index of refraction of the liquid specimen,
∂n/∂C is the first partial derivative of the index of refraction with respect to the concentration of the liquid specimen,
$V_{sig}$ is said reflected light beam digital voltage signal, and
ΔV is a difference between said reflected light beam digital voltage signal and an effective initial value of said reflected light beam digital voltage signal determined using said reference light beam digital voltage signal.

15. The method of claim 14, wherein:
step (a) comprises causing said measurement light beam to impinge on the surface of the liquid specimen at an angle which enhances percent change in reflectivity of the liquid surface with respect to the concentration of the liquid;
further comprising the additional steps of:
directing said reflected light beam into said signal photodiode; and
determining said effective initial value of said reflected light beam digital voltage signal based on:
said reference light beam digital voltage signal; and
a pair of constants determined from a linear regression for a data set comprising prior values of said reference light beam digital voltage signal and prior values of said reflected light beam digital voltage signal, said prior values of both of said signals being evaluated in a substantially unperturbed state.

16. An apparatus for non-contact measurement of temperature at a surface of a liquid specimen, said apparatus comprising:
(a) a light beam provider which produces a measurement light beam, having a measurement light beam intensity, which impinges on the surface of the liquid specimen and reflects back as a reflected light beam with a reflected light beam intensity related to both reflectivity, R, of the liquid surface and said measurement light beam intensity;
(b) a detector which receives said reflected light beam and determines said reflected light beam intensity; and
(c) means for determining the temperature of the liquid specimen from said reflected light beam intensity.

17. The apparatus of claim 16, wherein said light beam provider includes a coherent light source.

18. The apparatus of claim 17, wherein:
the liquid specimen is one of a single component liquid and a multi-component liquid with a substantially constant concentration;
said light beam provider produces a measurement light beam which impinges on the liquid surface at a near-normal angle of incidence; and
said determining means determines the temperature of the liquid specimen according to the formula:

$$\Delta R=(dR/dn)(\partial n/\partial T)\Delta T$$

where:
ΔR is a change in the reflectivity of the liquid specimen from a reference state as determined from said reflected light beam intensity and said measurement light beam intensity,
n is index of refraction of the liquid specimen,
dR/dn is first derivative of the reflectivity with respect to n, T is the temperature of the liquid specimen,
∂n/∂T is first partial derivative of n with respect to the temperature,
ΔT is a change in the temperature of the liquid specimen from a known initial value,
$R=((n-1)/(n+1))^2$, and
$dR/dn=4(n-1)/(n+1)^3$.

19. The apparatus of claim 17, wherein said light beam provider includes a beam splitter which provides a reference light beam and passes said measurement light beam to impinge on the surface of the liquid specimen, said reference light beam having a reference light beam intensity which is indicative of said measurement light beam intensity, wherein said determining means also receives said reference light beam and also uses said reference light beam intensity to determine the concentration of the liquid specimen, said reference light beam intensity being used to compensate for fluctuations in said measurement light beam intensity.

20. The apparatus of claim 19, wherein the liquid is one of a single component liquid and a multi-component liquid with a substantially constant concentration, and wherein said detector comprises:
(i) a signal photodetector which receives said reflected light beam and produces a reflected light beam signal indicative of said reflected light beam intensity; and
(ii) a reference photodetector which receives said reference light beam and produces a reference light beam signal indicative of said reference light beam intensity; and
wherein said determining means receives said reflected light beam signal and said reference light beam signal and determines the temperature of the liquid specimen based on:
index of refraction of the liquid,
first derivative of the index of refraction with respect to the temperature of the liquid,
said reflected light beam signal, and
a change of said reflected light beam intensity due to a change in the temperature of the liquid, said change of said reflected light beam intensity being determined using said reference light beam signal and said reflected light beam signal.

21. The apparatus of claim 20, wherein:
said determining means is a digital computer;
said signal photodetector comprises:
a signal photodiode which receives said reflected light beam and produces said reflected light beam signal;
a signal amplifier electrically coupled to said signal photodiode and electrically responsive to said reflected light beam signal, said signal amplifier producing a reflected light beam analog voltage signal; and
a signal digital voltmeter which receives said reflected light beam analog voltage signal and produces a reflected light beam digital voltage signal in response thereto, said reflected light beam digital voltage signal being input to said digital computer;
said reference photodetector comprises:
a reference photodiode which receives said reference light beam and produces said reference light beam signal;
a reference amplifier electrically coupled to said reference photodiode and electrically responsive to said reference light beam signal, said reference amplifier producing a reference light beam analog voltage signal; and
a reference digital voltmeter which receives said reference light beam analog voltage signal and produces a reference light beam digital voltage signal in response thereto, said reference light beam digital voltage signal being input to said digital computer; and said digital computer determines the temperature of the liquid based on a temperature change $\Delta T$ from an initial temperature value, the temperature change $\Delta T$ being determined using the formula:

$$\Delta T=((n^2-1)(\Delta V))/(4(\partial n/\partial T)V_{sig})$$

where:
n is the index of refraction of the liquid specimen,
$\partial n/\partial T$ is the first partial derivative of the index of refraction with respect to the temperature of the liquid specimen,
$V_{sig}$ is said reflected light beam digital voltage signal, and
$\Delta V$ is a difference between said reflected light beam digital voltage signal and an effective initial value of said reflected light beam digital voltage signal determined using said reference light beam digital voltage signal.

22. The apparatus of claim 21, wherein the light beam provider filter comprises:
a first mirror which directs said measurement light beam onto the surface of the liquid specimen at an angle which enhances percent change in reflectivity of the liquid surface with respect to the temperature of the liquid;
a second mirror which directs said reflected light beam into said signal photodiode; and
a correlator which determines said effective initial value of said reflected light beam digital voltage signal based on:
said reference light beam digital voltage signal; and
a pair of constants determined from a linear regression for a data set comprising prior values of said reference light beam digital voltage signal and prior values of said reflected light beam digital voltage signal, said prior values of both of said signals being evaluated in a substantially unperturbed state.

23. The apparatus of claim 16, further comprising a container which contains the liquid specimen.

24. A method for non-contact measurement of temperature at a surface of a liquid specimen, said method comprising the steps of:
(a) causing a measurement light beam having a measurement light beam intensity to impinge on the surface of the liquid specimen and to reflect back from the surface as a reflected light beam with a reflected light beam intensity related to both reflectivity, R, of the liquid specimen surface and said measurement light beam intensity;
(b) detecting said reflected light beam and measuring said reflected light beam intensity; and
(c) determining the temperature of the liquid specimen based on said reflected light beam intensity.

25. The method of claim 24, further comprising the additional step of providing a coherent light beam as the measurement light beam.

26. The method of claim 25, wherein:
the liquid specimen is one of a single component liquid and a multi-component liquid with a substantially constant concentration;
in step (a), said measurement light beam is caused to impinge on the surface of the liquid specimen at a near-normal angle of incidence; and step (c) comprises determining the temperature of the liquid specimen according to the formula:

$$\Delta R=(dR/dn)(\partial n/\partial T)\Delta T$$

where:
$\Delta R$ is a change in the reflectivity of the liquid from a reference state as determined from said reflected light beam intensity and said measurement light beam intensity,
n is index of refraction of the liquid specimen,
dR/dn is first derivative of the reflectivity with respect to n,
T is the temperature of the liquid,
$\partial n/\partial T$ is first partial derivative of n with respect to the temperature,
$\Delta T$ is a change in the temperature of the liquid from a known initial value,
$R=((n-1)/(n+1))^2$, and
$dR/dn=4(n-1)/(n+1)^3$.

27. The method of claim 26, further comprising the additional steps of:
(d) splitting a light beam into a reference light beam and said measurement light beam, said reference light beam having a reference light beam intensity which is directly proportional to said measurement light beam intensity;
(e) detecting said reference light beam and measuring said reference light beam intensity; and
(f) using said reference light beam intensity to compensate for fluctuations in the intensity of the measurement light beam when determining the concentration of the liquid specimen.

28. The method of claim 27, wherein:
the liquid specimen is one of a single component liquid and a multi-component liquid with a substantially constant concentration;
step (b) comprises receiving said reflected light beam in a signal photodetector which produces a reflected light beam signal indicative of the intensity of said reflected light beam; and
step (e) comprises receiving said reference light beam in a reference photodetector which produces a reference light beam signal indicative of the intensity of said reference light beam;
further comprising the additional step of providing a computer which receives said reflected light beam signal and said reference light beam signal and which performs steps (c) and (f) to determine the temperature of the liquid specimen based on:
index of refraction of the liquid specimen,
first derivative of the index of refraction with respect to the temperature of the liquid specimen,
said reflected light beam signal, and
a change of said reflected light beam intensity due to a change in the temperature of the liquid specimen, said change of said reflected light beam intensity being determined using said reference light beam signal and said reflected light beam signal.

29. The method of claim 28, wherein:
step (b) comprises providing said signal photodetector as a signal photodetector assembly comprising:

a signal photodiode which receives said reflected light beam and produces said reflected light beam signal;

a signal amplifier electrically coupled to said signal photodiode and electrically responsive to said reflected light beam signal, said signal amplifier producing a reflected light beam analog voltage signal; and a signal digital voltmeter which receives said reflected light beam analog voltage signal and produces a reflected light beam digital voltage signal in response thereto, said reflected light beam digital voltage signal being input to said digital computer;

step (e) comprises providing said reference photodetector as a reference photodetector assembly comprising:

a reference photodiode which receives said reference light beam and produces said reference light beam signal;

a reference amplifier electrically coupled to said reference photodiode and electrically responsive to said reference light beam current signal, said reference amplifier producing a reference light beam analog voltage signal;

a reference digital voltmeter which receives said reference light beam analog voltage signal and produces a reference light beam digital voltage signal in response thereto, said reference light beam digital voltage signal being input to said digital computer;

and said step of providing said computer comprises providing a digital computer which determines the temperature of the liquid based on a temperature change $\Delta T$ from an initial temperature value, the temperature change $\Delta T$ being determined using the formula:

$$\Delta T = ((n^2 - 1)(\Delta V))/(4(\partial n/\partial T)V_{sig})$$

where:

n is the index of refraction of the liquid specimen, $\partial n/\partial T$ is the first partial derivative of the index of refraction with respect to the temperature of the liquid specimen, $V_{sig}$ is said reflected light beam digital voltage signal, and $\Delta V$ is a difference between said reflected light beam digital voltage signal and an effective initial value of said reflected light beam digital voltage signal determined using said reference light beam digital voltage signal.

30. The method of claim 29, wherein:

step (a) comprises causing said measurement light beam to impinge on the surface of the liquid specimen at an angle which enhances percent change in reflectivity of the liquid specimen surface with respect to the temperature of the liquid;

further comprising the additional steps of:

directing said reflected light beam into said signal photodiode; and determining said effective initial value of said reflected light beam digital voltage signal based on:

said reference light beam digital voltage signal; and a pair of constants determined from a linear regression for a data set comprising prior values of said reference light beam digital voltage signal and prior values of said reflected light beam digital voltage signal, said prior values of both of said signals being evaluated in a substantially unperturbed state.

* * * * *

UNITED STATES PATENT AND TRADEMARK OFFICE
CERTIFICATE OF CORRECTION

PATENT NO. : 6,304,328 B1
DATED : October 16, 2001
INVENTOR(S) : Jon P. Longtin

It is certified that error appears in the above-identified patent and that said Letters Patent is hereby corrected as shown below:

Column 2,
Line 57, "=" should read -- $\cong$ --

Column 3,
Line 11, "=" should read -- $\cong$ --

Column 6,
Line 10, "=" should read -- $\cong$ --

Column 8,
Line 1, "out" should read -- art --
Line 2, "greater, accuracy," should read -- greater accuracy, --
Line 66, "$V_{sigj}$" should read -- $V_{sig,j}$ --
Line 67, "$V_{refj}$" should read -- $V_{ref,j}$ --

Column 10,
Line 14, "=" should read -- $\cong$ --
Line 31, "(8)" should be moved flush right
Line 32, "(9)" should be moved flush right Column 13,
Line 43, "$\Delta$" should read -- $\alpha$ --

Column 15,
Equation (13); "$\frac{dn}{dC}$" should read -- $\frac{\partial n}{\partial C}$ --

UNITED STATES PATENT AND TRADEMARK OFFICE
CERTIFICATE OF CORRECTION

PATENT NO. : 6,304,328 B1
DATED : October 16, 2001
INVENTOR(S) : Jon P. Longtin

It is certified that error appears in the above-identified patent and that said Letters Patent is hereby corrected as shown below:

<u>Column 21,</u>
Line 16, "=" should read -- ≅ --
Line 26, "oft he" should read -- of the --

<u>Column 23,</u>
Line 37, "=" should read -- ≅ --

<u>Column 25,</u>
Line 58, "=" should read -- ≅ --

<u>Column 28,</u>
Line 4, "=" should read -- ≅ --

Signed and Sealed this

Tenth Day of June, 2003

JAMES E. ROGAN
*Director of the United States Patent and Trademark Office*

UNITED STATES PATENT AND TRADEMARK OFFICE
CERTIFICATE OF CORRECTION

PATENT NO.   : 6,304,328 B1
DATED        : October 16, 2001
INVENTOR(S)  : Jon P. Longtin It is certified that error appears in the above-identified patent and that said Letters Patent is hereby corrected as shown below:

<u>Column 27,</u>
Line 23, "filter" should read -- further --

Signed and Sealed this

Twelfth Day of August, 2003

JAMES E. ROGAN
*Director of the United States Patent and Trademark Office*